United States Patent
Kool

(10) Patent No.: US 7,473,683 B2
(45) Date of Patent: Jan. 6, 2009

(54) NONPOLAR THYMIDINE ANALOGS

(75) Inventor: Eric Todd Kool, Stanford, CA (US)

(73) Assignee: The Board of Trustees of the Leland Stanford Junior University, Palo Alto, CA (US)

(*) Notice: Subject to any disclaimer, the term of this patent is extended or adjusted under 35 U.S.C. 154(b) by 141 days.

(21) Appl. No.: 11/519,385

(22) Filed: Sep. 11, 2006

(65) Prior Publication Data

US 2007/0065360 A1 Mar. 22, 2007

Related U.S. Application Data

(60) Provisional application No. 60/717,153, filed on Sep. 14, 2005.

(51) Int. Cl.
*A01N 43/04* (2006.01)
*A61K 31/70* (2006.01)

(52) U.S. Cl. .................................. 514/23; 536/1.11

(58) Field of Classification Search ............. None
See application file for complete search history.

(56) References Cited

U.S. PATENT DOCUMENTS

| | | | |
|---|---|---|---|
| 4,458,066 A | 7/1984 | Caruthers et al. |
| 4,755,619 A | 7/1988 | Creighton et al. |
| 6,790,841 B2 | 9/2004 | Zemlicka et al. |
| 6,803,371 B2 | 10/2004 | Gray et al. |
| 6,809,083 B1 | 10/2004 | Mueller et al. |
| 6,809,109 B2 | 10/2004 | Rodgers et al. |
| 6,815,542 B2 | 11/2004 | Hong et al. |
| 6,818,633 B2 | 11/2004 | Balzarini et al. |
| 6,825,177 B2 | 11/2004 | Uckun et al. |
| 6,825,337 B2 | 11/2004 | Watt |
| 6,828,149 B2 | 12/2004 | Freier |
| 6,828,151 B2 | 12/2004 | Borchers et al. |

OTHER PUBLICATIONS

Wang et al. Nucleosides, Nucleotides & Nucleic Acids (2001), vol. 20, pp. 11-40.*
Delaney, J., et al., "High-fidelity in vivo replication of DNA base shape mimics without Watson-Crick hydrogen bonds," (2003) PNAS, 100(8):4469-4473.
Drotschmann, K., et al., "Asymmetric recognition of DNA local distortion," (2001) The Journal of Biological Chemistry, 276(49):46225-46229.
Francis, A., et al., "Probing the requirements for recognition and catalysis in Fpg and MutY with nonpolar adenine isosteres," (2003) J. Am. Chem. Soc., 125:16235-16242.
Guckian, K., et al., "Solution structure of a DNA duplex containing a replicable difluorotoluene-adenne pair," (1998) Nature Structural Biology, 5(11):954-958.
Kool, E., "Active site tightness and substrate fit in DNA replication," (2002) Annu. Rev. Biochem., 71:191-219.
Kool, E., "Hydrogen bonding, base stacking, and steric effects in DNA replication," (2001) Annu. Rev. Biophys. Biomol. Struct. 30:1-22.
Kool, E., et al., "Mimicking the structure and function of DNA: insights into DNA stability and replication," (2000) Angew. Chem. Int. Ed., 39:990-1009.
Moran, S., et al., "A thymidine triphosphate shape analog lacking Watson-Crick pairing ability is replicated with high sequence selectivity," (1997) PNAS, 94:10506-10511.
Moran, S., et al., "Difluorotoluene, a nonpolar isostere for thymine, codes specifically and efficiently for adenine in DNA replication," (1997) J. Am. Chem. Soc., 119:2056-2057.
Rausch, J., et al., "Hydrolysis of RNA/DNA hybrids containing nonpolar pyrimidine isosteres defines regions essential for HIV type 1 polypurine tract selection," (2003) PNAS, 100(20):11279-11284.
Rutten, T., et al., "A 60-kDa plant microtubule-associated protein promotes the growth and stabilization of neurotubules in vitro," (1997) PNAS, 94:4469-4474.
Schofield, M., et al., "The phe-x-glu DNA binding motif of MutS," (2001) The Journal of Biological Chemistry, 276 (49):45505-45508.
Schweitzer, B., et al., "Hydrophobic, non-hydrogen-bonding bases and base pairs in DNA," (1995) J. Am. Chem. Soc., 117(7):1863-1872.
Schweitzer, B., et al., "Aromatic non-polar nucleosides as hydrophobic isosteres of pyrimidine and purine nucleosides," (1994) J. Org. Chem., 59:7238-7242.

* cited by examiner

Primary Examiner—Patrick T Lewis
(74) Attorney, Agent, or Firm—Bozicevic, Field & Francis LLP; Pamela J. Sherwood

(57) ABSTRACT

Nonpolar thymidine analogs are provided comprising a dihalogenated or trihalogenated base of the structure:

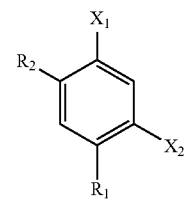

where $R_1$ is a sugar moiety;
$R_2$ is H or $CH_3$; an imaging moiety or a cytotoxic moiety and
$X_1$ and $X_2$ are independently selected from I, Cl, Br, and F, with the proviso that not more than one F will be present at these positions.

19 Claims, 8 Drawing Sheets

| bond length | C-H (1) | C-F (2) | C-Cl (3) | C-Br (4) | C-I (5) | C-O (6) |
|---|---|---|---|---|---|---|
| calculated (Å)[a] | 1.10 | 1.34 | 1.69 | 1.87 | 1.97 | 1.22 |
| crystal structure (Å)[b] | -- | 1.37 (C2-F, C4-F) | 1.75 (C2-Cl), 1.74 (C4-Cl) | -- | -- | 1.21 (C2-O), 1.23 (C4-O) |

A)

B)

| | dihedral angles [°] | | | | | |
|---|---|---|---|---|---|---|
| | C6-C2' | O4'-C3' | C1'-C4' | C2'-C5' | C(N)1-C3' | C3'-C1' |
| 6 | -79.5 | +28.4 | -37.2 | -87.3 | +147.8 | -16.8 |
| 2 | -97.6 | +32.2 | -36.7 | -91.5 | +153.2 | -9.0 |
| 3 | -90.1 | +31.7 | -32.5 | -95.5 | +152.4 | -2.4 |

A) 5'-CTTTTCXTTCTT    X = T, H, F, L, B, I
3'-GAAAAGYAAGAA   Y = A, C, G, T

B) 5'-CTTTTCYTTCTT   Y = A, C, G, T
3'-GAAAAGXAAGAA   X = T, H, F, L, B, I

NONPOLAR THYMIDINE ANALOGS

This invention was made with Government support under contract GM072705 awarded by the National Institutes of Health. The Government has certain rights in this invention.

BACKGROUND OF THE INVENTION

The physical and chemical factors that allow polynucleotides to perform their functions in the cell have been studied for several decades. Recent advances in the synthesis and manipulation of polynucleotides have allowed this field to move ahead especially rapidly during the past fifteen years. One of the most common chemical approaches to the study of interactions involving has been the use of nucleoside base analogs in which functional groups are added, deleted, blocked, or rearranged.

Such nucleoside analogs may be useful as in providing specific alterations to reaction kinetics; properties to oligonucleotide probes for diagnostic applications; to alter the properties of antisense RNA and RNAi; and in the synthesis and purification of oligonucleotides. Nucleoside analogs may also find use as metabolic inhibitors of viruses and proliferating cells, including tumor cells. Currently a number of nucleoside based drugs are being used to treat human diseases, including AIDS, against various cancers and for various systemic diseases resulting from inappropriate immune responses.

Among the uses of oligonucleotides are methods of inhibiting gene expression with antisense oligonucleotides complementary to a specific target messenger RNA (mRNA) sequences. Oligonucleotides also have found use in diagnostic tests performed using biological fluids, tissues, intact cells or isolated cellular components. For diagnostics, oligonucleotides and oligonucleotide analogs can be used in cell free systems, in vitro, ex vivo or in vivo.

Oligonucleotides and nucleosides are also widely used as research reagents. They are useful for understanding the function of many other biological molecules as well as in the preparation of such other biological molecules. For example, oligonucleotides serve as primers in the reactions associated with polymerase chain reaction (PCR), which reactions are now widely used in forensics, paleontology, evolutionary studies and genetic counseling, to name just a few.

Nucleoside analogues that lack specific hydrogen bonding groups have proven useful in a number of biological contexts for probing the physical and chemical importance of such electrostatically charged moieties. For example, Strazewski and Tamm reported over two decades ago the synthesis of pyrimidine analogues lacking one of three hydrogen bonding groups, and investigated their substrate abilities with DNA polymerase enzymes. In another example, McLaughlin reported nucleobases with single functional groups deleted, and described their properties in pairing in DNA. Taking this approach to its logical limit, all Watson-Crick hydrogen bonding groups were removed in nucleoside analogues, preparing several "nonpolar nucleoside isosteres", which maintain the steric size and shapes of natural nucleobases but lack polar functionality (Schweitzer and Kool (1994) J. Org. Chem. 59, 7238; Schweitzer and Kool (1995) J. Am. Chem. Soc. 117, 1863; Kool et al. (2000) Angew. Chem. Int. Ed. 39, 990. Examples included 4-methyl-aza-benzimidazole, an adenine mimic, and 2,4-difluorotoluene, a thymine mimic.

Nonpolar nucleoside isosteres have proven useful in probing the recognition of DNA by other nucleic acids, and in studies of the physical origins of DNA curvature. Biophysical studies have shown that thymine and adenine isosteres destabilize DNAs in which they are substituted, unless they are in a terminal position, in which case they can be strongly stabilizing, due to their avid stacking with natural DNA bases. Structural studies have shown that, despite the destabilization when present at non-terminal locations, thymine and adenine mimics show essentially the same structures as the natural congeners.

Nonpolar nucleoside mimics have also been increasingly useful of late in the study of protein-DNA and enzyme-DNA recognition. Studies have been reported with purine and pyrimidine mimics in a number of DNA repair enzymes, including MutY (Guckian et al. (1998) Nature Structural biology 5, 954); fpg; (Francis et al. (2003) J. Am. Chem. Soc. 125, 16235), MutS and homologues (Schofield et al. (2001) J. Biol. Chem. 276, 45505; Drotschmann et al. (2001) J. Biol. Chem. 276, 46225; and in polypurine tract recognition by HIV reverse transcriptase (Rausch et al. (2003) Proc. Natl. Acad. Sci. USA 100, 11279). Those studies have shed light on the relative importance of hydrogen bonding and steric interactions to these enzymes' biochemical activities.

In addition to this, nonpolar nucleoside isosteres have proven broadly useful in the study of DNA replication by a wide variety of polymerase enzymes. Such nonpolar analogues were first reported in 1997 to act as surprisingly strong substrates for DNA polymerase I, (Moran et al. (1997) J. Am. Chem. Soc. 119, 2056; Moran et al. (1997) Proc. Natl. Acad. Sci. USA 94, 10506) leading to the conclusion that at least some replicative DNA polymerases function well in synthesis of a base pair without Watson-Crick hydrogen bonds. This has since been confirmed by a number of studies of varied polymerase enzymes in vitro, and recently in living bacterial cells as well. The discovery of the lack of a hydrogen bonding requirement in replication has led to design other non-isosteric DNA base pairs for expansion of the genetic information-encoding system.

A high fidelity for DNA replication is required to maintain proper transfer of genetic information during cell division. The first and most influential step that determines this fidelity is synthesis of a new base pair by a replicative DNA polymerase. This choice, which occurs dozens of times per second, involves the selection of one nucleotide among four for insertion into the growing primer strand, opposite each DNA template base as it is addressed in turn. In eukaryotes, the replicative enzymes are DNA polymerases delta, alpha, and epsilon. In eubacteria, the replicative polymerases are Pol III, which synthesizes the leading strand, and Pol I, which assists Pol III with the lagging strand. These latter polymerases make an error (synthesis of a mismatched pair) only once in ca. $10^4$-$10^5$ nucleotide insertions.

The biophysical origin of this fidelity is a long-standing topic of research on polymerases. Early studies often focused on matching of Watson-Crick hydrogen bonds; however, it was subsequently recognized that at the terminus of DNA, base pairing selectivity in the absence of enzymes is too low to account for the observed enzymatic fidelity. More recently, it has been shown that a nonpolar isostere of thymine (difluorotoluene) can be replicated with nearly wild-type fidelity despite its lack of hydrogen bonding ability (Moran et al. (1997) *J. Am. Chem. Soc.* 119, 2056-2057; Moran et al. (1997) *Proc. Natl. Acad. Sci. USA* 94, 10506-10511; Delaney et al. (2003) *Proc. Natl. Acad. Sci. USA* 100, 4469-4473). Such observations, in conjunction with structural and mutational studies, have led to the hypothesis that geometry of DNA base pairs may be regulated by a close fit in polymerase active sites (Kool (2002) *Ann. Rev. Biochem.* 71, 191-219; Kool (2001) *Annu. Rev. Biophys. Biomol. Struct.* 30, 1-33; Goodman (1997) *Proc. Natl. Acad. Sci. USA* 94, 4469-4473).

The development of novel nucleoside analogs is of interest for a variety of research and therapeutic uses. The present invention addresses this issue.

SUMMARY OF THE INVENTION

Compositions of nonpolar thymidine analogs are provided. The analogs of the invention are good substrates for a variety of polymerases, and certain analogs are better polymerase substrates than previously known nucleoside analogs. The analogs of the invention find use as template and/or substrate in enzymatic polynucleotide polymerization reactions, e.g. RNA polymerization, DNA polymerization, etc., including isothermal amplification reactions. Other nucleoside analogs of the invention may find use as therapeutic agents to inhibit polymerization reactions, e.g. as antiviral agents, anti-proliferative agents; and as imaging agents.

Compositions of the invention include glycosides comprising the nonpolar thymidine analogs; mono-, di-, and triphosphate esters thereof; derivatives suitable for in vitro synthetic reactions; and oligonucleotides wherein at least one nucleoside is a nonpolar analog of the invention. Oligonucleotides comprising one or more nucleoside analogs of the invention may have altered properties, including increased resistance to degradation, an increase in hydrophobicity, and altered stability of double or triple stranded helices. Such oligonucleotides may find use as anti-sense reagents, as RNAi agents, as primers and templates for polymerization reactions, and the like.

In one embodiment, the nucleoside or nucleotide analogs of the invention are used as a substrate and/or template in polymerization reactions, which reactions may be in vitro or in vivo. Polymerization reactions of interest include reactions catalyzed by polymerases, e.g. DNA dependent DNA polymerase, DNA dependent RNA polymerase, RNA dependent DNA polymerase, RNA dependent RNA polymerase, and the like. The analogs of the invention have been shown to be effective as substrates for a variety of eukaryotic and prokaryotic polymerases, including Pol I, reverse transcriptase, T7 polymerase, Taq polymerase, Pol α, Pol β, etc. Exemplary reactions include cDNA synthesis; isothermal amplification reactions; siRNA synthesis; and the like.

For amplification reactions, nucleotide analogs may be provided as a substrate. In addition, primers may comprise the nucleoside analogs of the invention, or may lack such analogs. In reactions where the terminal nucleosides of the primers lack such analogs, and the analogs are used as a substrate for DNA polymerase, the resulting double helix is destabilized relative to native DNA, and can be denatured at reduced temperatures. Where the terminal nucleosides of one or more primers comprise analogs of the invention, the double helix may be stabilized relative to native DNA.

In other embodiments of the invention, the nucleoside or nucleotide analogs of the invention are utilized as a substrate to inhibit polymerization reactions, e.g. as an anti-viral agent, anti-proliferative agent, etc. In such analogs, the ribose, deoxyribose, dideoxyribose, etc. sugars may comprise modifications at the 2', 3', 4' and 5' positions, which modifications terminate or otherwise inhibit polymerization. The preference of polymerases for the analog nucleosides of the invention over native nucleosides provides for enhanced inhibition of the targeted reaction, relative to compounds comprising native thymidine or uracil.

DETAILED DESCRIPTION OF THE INVENTION

Figure 1:
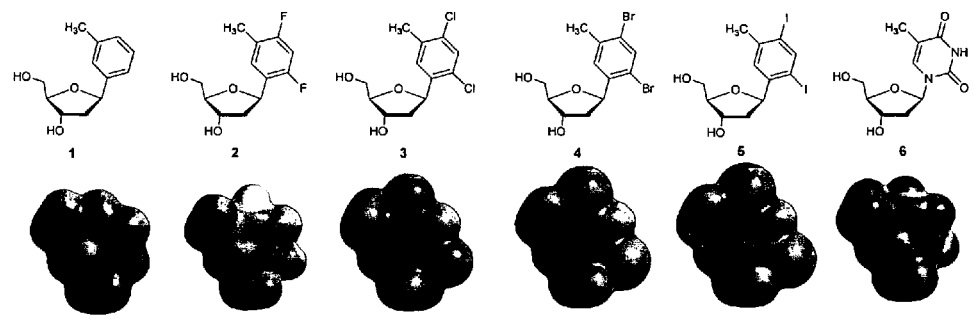
FIG. 1A-1B. Structures of the thymidine analogues, designed to have gradually increasing steric demand. A) Space-filling models of the analogues with methyl groups at the point of attachment to deoxyribose, calculated electrostatic potentials mapped on the van der Waals surfaces (electrostatic scale: −50 to 30). B) PM3-calculated bond lengths for the 2,4-substituents, which range in size from H to I (Spartan '02, Wavefunction, Inc.). Calculated thymine bond lengths are shown for comparison. Also shown are corresponding bond lengths from crystal structures of three of the compounds.

Nonpolar nucleoside, nucleotide and oligonucleotide analogs comprising glycosides of specific dihalogenated toluene and benzene moieties or trihalogenated benzene moieties are provided herein. These previously undescribed molecules are shown herein to be efficient substrates for polymerases, and find a variety of uses in polymerization reactions. Analogs of the invention may be introduced at any position in an oligonucleotide, e.g. 5' terminus, 3' terminus, or internal positions, e.g. through synthetic reactions. Oligonucleotides may be provided in a single stranded or double stranded form.

The analogs of the invention lack the ability to form hydrogen bonds in base pairing interactions. It was therefore surprising that they proved to be good mimics for thymidine, as hydrogen bonding has been believed to be important to thymidine activity. Given the lack of hydrogen bonds and increased size relative to thymidine, it was particularly unexpected that the analogs were good polymerase substrates; some analogs proved even better substrates than thymidine itself.

The analogs of the invention, as demonstrated herein, are active substrates for polymerases in vitro and in vivo. As such, they find use as probes for the roles of hydrogen bonding, electrostatics, and molecular size and shape on the biochemical and biological properties of thymidine. As polymerase substrates, the analogs may also exhibit anticancer or antiviral activity, particularly when provided as a glycoside of an inhibitory moiety, e.g. dideoxy sugars, azido modified sugars, and the like. The analogs can also induce therapeutically effective mutations, may interfere with cellular DNA repair mechanisms, and may interfere with cellular nucleotide metabolism pathways.

The analogs are not repaired by standard glycosidase enzymes, and when incorporated into a polynucleotide, the analogs can be used to slow the rate at which the polynucleotide is degraded by enzymes.

The analogs will increase the hydrophobicity (or lower the polarity) of any DNA or RNA they are incorporated into. This may aid in purification and/or in increasing their cellular uptake. Double stranded helices will be destabilized by incorporation of the analogs, which property finds use in separation, amplification schemes, e.g. isothermal amplifications; and the like.

Compounds of interest include glycosides, nucleosides, nucleotides and oligonucleotides comprising the nucleoside base analogs. Any of such compounds may be provided in combination with a pharmaceutically acceptable excipient, e.g. for use as a substrate or template in polymerization reactions, as an antisense reagent; as a metabolic inhibitor; as a diagnostic probe; and the like.

Before the subject invention is described further, it is to be understood that the invention is not limited to the particular embodiments of the invention described below, as variations of the particular embodiments may be made and still fall within the scope of the appended claims. It is also to be understood that the terminology employed is for the purpose of describing particular embodiments, and is not intended to be limiting. Instead, the scope of the present invention will be established by the appended claims.

In this specification and the appended claims, the singular forms "a," "an" and "the" include plural reference unless the context clearly dictates otherwise. Unless defined otherwise, all technical and scientific terms used herein have the same meaning as commonly understood to one of ordinary skill in the art to which this invention belongs.

Where a range of values is provided, it is understood that each intervening value, to the tenth of the unit of the lower limit unless the context clearly dictates otherwise, between the upper and lower limit of that range, and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood to one of ordinary skill in the art to which this invention belongs. Although any methods, devices and materials similar or equivalent to those described herein can be used in the practice or testing of the invention, the preferred methods, devices and materials are now described.

All publications mentioned herein are incorporated herein by reference for the purpose of describing and disclosing those components that are described in the publications that might be used in connection with the presently described invention.

As used herein, compounds which are "commercially available" may be obtained from standard commercial sources including Acros Organics (Pittsburgh Pa.), Aldrich Chemical (Milwaukee Wis., including Sigma Chemical and Fluka), Apin Chemicals Ltd. (Milton Park UK), Avocado Research (Lancashire U.K.), BDH Inc. (Toronto, Canada), Bionet (Cornwall, U.K.), Chemservice Inc. (West Chester Pa.), Crescent Chemical Co. (Hauppauge N.Y.), Eastman Organic Chemicals, Eastman Kodak Company (Rochester N.Y.), Fisher Scientific Co. (Pittsburgh Pa.), Fisons Chemicals (Leicestershire UK), Frontier Scientific (Logan Utah), ICN Biomedicals, Inc. (Costa Mesa Calif.), Key Organics (Cornwall U.K.), Lancaster Synthesis (Windham N.H.), Maybridge Chemical Co. Ltd. (Cornwall U.K.), Parish Chemical Co. (Orem Utah), Pfaltz & Bauer, Inc. (Waterbury Conn.), Polyorganix (Houston Tex.), Pierce Chemical Co. (Rockford Ill.), Riedel de Haen AG (Hannover, Germany), Spectrum Quality Product, Inc. (New Brunswick, N.J.), TCI America (Portland Oreg.), Trans World Chemicals, Inc. (Rockville Md.), Wako Chemicals USA, Inc. (Richmond Va.); Molecular Probes (Eugene, Oreg.); Applied Biosystems, Inc. (Foster City, Calif.); and Glen Research (Sterling, Va.).

As used herein, "suitable conditions" for carrying out a synthetic step are explicitly provided herein or may be discerned by reference to publications directed to methods used in synthetic organic chemistry. The reference books and treatise set forth above that detail the synthesis of reactants useful in the preparation of compounds of the present invention, will also provide suitable conditions for carrying out a synthetic step according to the present invention.

As used herein, "methods known to one of ordinary skill in the art" may be identified though various reference books and databases. Suitable reference books and treatise that detail the synthesis of reactants useful in the preparation of compounds of the present invention, or provide references to articles that describe the preparation, include for example, "Synthetic Organic Chemistry", John Wiley & Sons, Inc., New York; S. R. Sandier et al., "Organic Functional Group Preparations," 2nd Ed., Academic Press, New York, 1983; H. O. House, "Modern Synthetic Reactions", 2nd Ed., W.A. Benjamin, Inc. Menlo Park, Calif. 1972; T. L. Gilchrist, "Heterocyclic Chemistry", 2nd Ed., John Wiley & Sons, New York, 1992; J. March, "Advanced Organic Chemistry: Reactions, Mechanisms and Structure", 4th Ed., Wiley-Interscience, New York, 1992. Specific and analogous reactants may also be identified through the indices of known chemicals prepared by the Chemical Abstract Service of the American Chemical Society, which are available in most public and university libraries, as well as through on-line databases (the American Chemical Society, Washington, D.C., may be contacted for more details). Chemicals that are known but not commercially available in catalogs may be prepared by custom chemical synthesis houses, where many of the standard chemical supply houses (e.g., those listed above) provide custom synthesis services.

"Stable compound" and "stable structure" are meant to indicate a compound that is sufficiently robust to survive isolation to a useful degree of purity from a reaction mixture, and formulation into an efficacious therapeutic agent.

"Optional" or "optionally" means that the subsequently described event of circumstances may or may not occur, and that the description includes instances where said event or circumstance occurs and instances in which it does not. For example, "optionally substituted aryl" means that the aryl radical may or may not be substituted and that the description includes both substituted aryl radicals and aryl radicals having no substitution. The term lower alkyl will be used herein as known in the art to refer to an alkyl, straight, branched or cyclic, of from about 1 to 6 carbons.

"Pharmaceutically acceptable carrier, diluent or excipient" includes without limitation any adjuvant, carrier, excipient, glidant, sweetening agent, diluent, preservative, dye/colorant, flavor enhancer, surfactant, wetting agent, dispersing agent, suspending agent, stabilizer, isotonic agent, solvent, or emulsifier which has been approved by the United States Food and Drug Administration as being acceptable for use in humans or domestic animals.

"Pharmaceutically acceptable salt" includes both acid and base addition salts. "Pharmaceutically acceptable acid addition salt" refers to those salts which retain the biological effectiveness and properties of the free bases, which are not biologically or otherwise undesirable, and which are formed with inorganic acids such as hydrochloric acid, hydrobromic acid, sulfuric acid, nitric acid, phosphoric acid and the like, and organic acids such as acetic acid, trifluoroacetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like.

"Pharmaceutically acceptable base addition salt" refers to those salts that retain the biological effectiveness and properties of the free acids, which are not biologically or otherwise undesirable. These salts are prepared from addition of an inorganic base or an organic base to the free acid. Salts derived from inorganic bases include, but are not limited to, the sodium, potassium, lithium, ammonium, calcium, magnesium, iron, zinc, copper, manganese, aluminum salts and the like. Preferred inorganic salts are the ammonium, sodium, potassium, calcium, and magnesium salts. Salts derived from organic bases include, but are not limited to, salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, 2-dimethylaminoethanol, 2-diethylaminoethanol, dicyclohexylamine, lysine, arginine, histidine, caffeine, procaine, hydrabamine, choline, betaine, ethylenediamine, glucosamine, methylglucamine, theobromine, purines, piperazine, piperidine, N-ethylpiperidine, polyamine resins and the like. Particularly preferred organic bases are isopropylamine, diethylamine, ethanolamine, trimethylamine, dicyclohexylamine, choline and caffeine.

The compounds of the invention, or their pharmaceutically acceptable salts may contain one or more asymmetric centers and may thus give rise to enantiomers, diastereomers, and other stereoisomeric forms that may be defined, in terms of absolute stereochemistry, as (R)- or (S)- or, as (D)- or (L)- for amino acids. The present invention is meant to include all such possible isomers, as well as, their racemic and optically pure forms. Optically active (+) and (−), (R)- and (S)-, or (D)- and (L)-isomers may be prepared using chiral synthons or chiral reagents, or resolved using conventional techniques, such as reverse phase HPLC. When the compounds described herein contain olefinic double bonds or other centers of geometric asymmetry, and unless specified otherwise, it is intended that the compounds include both E and Z geometric isomers. Likewise, all tautomeric forms are also intended to be included.

Compositions

Nucleoside analogs of interest are glycosides of dihalogenated toluene or benzene rings, or trihalogenated benzene rings. Also included are derivatives thereof, e.g. nucleotides, oligonucleotides, and the like; which may include various modifications to the sugar and phosphate backbone, as is known in the art. Included in the invention are compounds comprising a structure as set forth below:

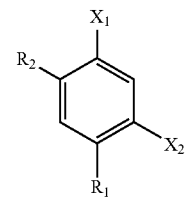

I where $R_1$ is a sugar moiety, including any pentose or hexose sugars, particularly ribose and deoxyribose, which may be in an N-glycoside or C-glycoside configuration, having a D- or L stereochemistry;

$R_2$ is H, $CH_3$, or a cytotoxic or imaging moiety. Where $R_2$ is an imaging or cytotoxic moiety, an isotope of iodine or fluorine may be selected as $R_2$.

$X_1$ and $X_2$ are independently selected from I, Cl, Br, and F, with the proviso that not more than one F will be present.

Any isotope of I, Cl, Br, and F may be used, including, without limitation, $^{18}F$, $^{19}F$, $^{123}I$, $^{124}I$, $^{125}I$, $^{127}I$, $^{128}I$, and $^{131}I$.

Some specific compounds of interest include the following glycoside structures, where the ring numbering is that of formula I, i.e. the sugar is attached at position 1. Compounds of interest include 2,4-dichlorotoluene; 2,4-dibromotoluene; 2-chloro,4-bromo-toluene; 2-chloro,4-fluoro-toluene; 2-bromo,4-chloro-toluene; 2-bromo,4-fluoro-toluene; 2-fluoro,4-chloro-toluene; 2-fluoro,4-bromo-toluene; 2,4-dichlorobenzene; 2,4-dibromobenzene; 2-chloro,4-bromo-benzene; 2-chloro,4-fluoro-benzene; 2-bromo,4-chloro-benzene; 2-bromo,4-fluoro-benzene; 2-fluoro,4-chloro-benzene; and 2-fluoro,4-bromo-benzene. Particularly efficient analogs for polymerization are 2-chloro-4-bromo-toluene and 2,4-dichlorotoluene. Dihalogenated toluene and trihalogenated benzene may serve as an analog for thymidine, while dihalogenated benzene is an analog of uracil.

As used herein, "nucleoside" means a base covalently attached to a sugar or sugar analog and which may contain a phosphate, phosphoroamidite, diphosphate, cyclic phosphate, triphosphate, phosphite or phosphine, where sugars include any pentose or hexose sugars, particularly ribose and deoxyribose, which may be in an N-glycoside or C-glycoside configuration, having a D- or L stereochemistry. Sugar modifications of interest include, without limitation, ribose, deoxyribose and dideoxyribose sugars comprising modifications at the 2', 3', 4' and 5' positions, particularly where the nucleoside is intended as a pharmaceutical agent, e.g. as an anti-viral or anti-proliferative drug. Some specific examples of modifications at the 2' and 3' position of sugar moieties are azido, OH, SH, $SCH_3$, F, OCN, $O(CH_2)n\ NH_2$, $O(CH_2)n\ CH_3$ where n is from 1 to about 10; $C_1$ to $C_{10}$ lower alkyl, substituted lower alkyl, alkaryl or aralkyl; Cl, Br, CN, $CF_3$, $OCF_3$, O—, S—, or N-alkyl; O—, S—, or N-alkenyl; $SOCH_3$, $SO_2$; $CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a conjugate; a reporter group; an intercalator; a group for improving the pharmacokinetic properties of an oligonucleotide; or a group for improving the pharmacodynamic properties of an oligonucleotide and other substituents having similar properties. For synthetic reactions, the analogs may be provided as a phosphoroamidite, H-phosphonate, etc.

The pentose moiety can be replaced by a hexose or an alternate structure such as a cyclopentane ring, a 6-member morpholino ring and the like. Nucleosides as defined herein are also intended to include a base linked to an amino acid and/or an amino acid analog having a free carboxyl group and/or a free amino group and/or protected forms thereof.

As used herein, "nucleotide" refers to a nucleoside having a phosphate, triphosphate, or phosphate analog group, particularly a nucleoside in which the 5'-hydroxyl group of a nucleoside is esterified with a phosphate, boranophosphate, or otherwise modified phosphate group.

In some embodiments of the invention, an oligonucleotide comprising one or more of the subject nonpolar nucleoside analogs of the invention is provided, internally, and/or at either or both of the 5' or 3' ends of a linear nucleic acid molecule. The subject base analogs may be present in more than one position in an RNA or DNA molecule. One or more base analogs may be incorporated within a stretch of sequence so that the DNA or RNA fragment is effectively tagged towards the middle of the molecule. The RNA or DNA sequence may comprise a linear, hairpin, dumbbell, circular, or branched conformation and may be single or double stranded. The term "oligonucleotide" refers to a polynucleotide formed from naturally occurring bases, such as purine and pyrimidine heterocycles, and furanosyl groups joined by native phosphodiester bonds, as well as synthetic species formed from naturally occurring subunits or their close homologs, and synthetic species comprising non-naturally occurring analogs (in addition to the nonpolar analog(s)) of bases, backbone and/or sugars.

Purines and pyrimidines other than those normally found in nature may also be included in oligonucleotides, in addition to the analogs of the invention. For example, deaza or aza purines and pyrimidines may be used in place of naturally purine or pyrimidine bases and pyrimidine bases having substituent groups at the 5- or 6-positions; purine bases may have altered or replacement substituent groups at the 2-, 6- or 8-positions.

Oligonucleotides may also comprise backbone modifications, including peptide nucleic acids (PNA), locked nucleic acids (LNA), etc., methylations, morpholino derivatives; phosphoroamidate derivatives; unusual base-pairing combinations such as the isobases isocytidine and isoguanidine and the like. Derivatives can also include 3' and 5' modifications such as capping.

As is used in the art, the term "oligonucleotide" usually refers to shorter molecules, usually of at least about 3 bases in length, more usually at least 4, 5, or 6 bases; for many embodiments of the invention, preferred oligonucleotides are at least 7 bases, at least 8 bases, at least 10 bases, at least 12 bases, and not more than about 100 bases in length, usually not more than about 50 bases in length, or any length range between any two of these lengths. The term "polynucleotide" may refer to any length of nucleic acid greater than a single base; although in many instances will be used to refer to molecules as present in living organisms, which range from about 50 bases in length to many megabases, in the case of genomic DNAs.

The oligonucleotide can be derived from a completely chemical synthesis process, such as a solid phase mediated chemical synthesis, or from a biological origin, such as through isolation from almost any species that can provide DNA or RNA, or from processes that involve the manipulation of nucleic acids by molecular biology tools, such as DNA replication, PCR amplification, reverse transcription, or from a combination of those processes. Modifications to introduce a nonpolar base analog of the invention may be used as a primer in a synthetic reaction, e.g. PCR; may be introduced at any position during in vitro or in vivo synthesis; and the like.

Modified oligonucleotides of the invention may be provided in solution, or bound to a substrate. One, a pair or a plurality of modified probes may be provided in any configuration. By "solid substrate" or "solid support" is meant any surface to which the probes of the invention are attached. A variety of solid supports or substrates are suitable for the purposes of the invention, including both flexible and rigid substrates. By flexible is meant that the support is capable of being bent, folded or similarly manipulated without breakage. Examples of flexible solid supports include nylon, nitrocellulose, polypropylene, polyester films, such as polyethylene terephthalate, etc. Rigid supports do not readily bend, and include glass, fused silica, quartz, acrylamide; plastics, e.g. polytetrafluoroethylene, polypropylene, polystyrene, polystyrene and sulfonated polystyrene-divinyl benzene, quaternized product of chloromethylated polystyrene-divinyl benzene, PEG-polystyrene, PEG, polycarbonate, and blends thereof, and the like; metals, e.g. gold, platinum, silver, and the like; etc. The substrates can take a variety of configurations, including planar surfaces, filters, fibers, membranes, beads, particles, dipsticks, sheets, rods, etc. The substrates can be prepared using any convenient means. One means of preparing the supports is to synthesize the probes, and then deposit them on the support surface. The probes can be deposited on the support using any convenient methodology, including manual techniques, e.g. by micropipette, ink jet, pins, etc., and automated protocols. The probes may also be covalently attached to the substrate, using methods known in the art. Alternatively, the probes can be synthesized on the substrate using standard techniques known in the art.

The nucleoside analogs of the invention may be incorporated into oligonucleotides by automated solid-phase methods such as phosphoroamidite reactions, using readily available reagents and equipment (see, for example, U.S. Pat. No. 4,458,066; or a review of the art in "Perspectives in Nucleoside and Nucleic Acid Chemistry"; ISBN: 3-90639-021-7, herein incorporated by reference). One such method is illustrated in Example 2, and in scheme 2. Alternatively, an H-phosphonate method of synthesis may be used.

Methods of Use

Nucleotides, oligonucleotides and polynucleotides comprising one or more of the subject analog nucleosides may be used in any of the techniques known in the art for such molecules, including use substrates for polymerization reactions including isothermal amplification reactions; as polymerization inhibitors, as probes in hybridization, as antisense probes for inhibition of expression; as RNAi for inhibition of expression; as a primer for amplification reactions; a primer for RNA synthesis, and the like. In one aspect, the presence of nonpolar nucleosides stabilizes the oligonucleotide, and therefore provides a stabilized oligonucleotide composition, and a method for stabilization by introduction of the nucleoside analog into an oligonucleotide.

Amplification reactions may be performed with one or two primers, where the primers may comprise native nucleosides, or may comprise the nucleoside analogs of the invention. The amplification reactions may be performed for at least about 1 cycle, and may be performed for 5, 10, 15, 20, 25, 30 cycles, or more. As used in this invention, "amplifying" means adding the appropriate reagents (i.e. primers with appropriate sequences, enzymes, polymerases, nucleotides including nucleotide analogs of the invention, buffers, etc.) to a sample in order to reproduce, generally in a sequential fashion, numerous copies of one or more nucleic acids present. One skilled in the art is familiar with various nucleic acid amplification reactions, such as the polymerase chain reaction resulting in amplified DNA. Various modifications of the basic amplification reactions, as known in the art, can also be employed with specific embodiments of this invention. The nature of the amplification reaction selected depends on various factors such as the original source of nucleic acids and the desired final products. There is, therefore, no limitation to the type of amplification reaction that can be employed during the "amplifying" step in the methods of this invention. The conditions used for "amplifying" will vary with the type of reaction selected.

The amplified product is used in various methods known in the art. Where the product is used as a probe, it may be labeled with a detectable marker, e.g. fluorochrome or biotin labeled nucleotide derivatives are incorporated by reaction with polymerase. Nucleotides may be obtained which are pre-labeled, where these nucleotides will become incorporated in the product. A wide variety of labeling techniques are well known to those skilled in the art and may be used in accordance with standard procedures (see, U.S. Pat. No. 4,755,619, which is incorporated herein by reference). Alternatively the probes may be labeled by end-labeling; etc.

Where the nucleoside analogs are incorporated in internal positions of an oligonucleotide or polynucleotide, there is a decrease in stability upon formation of a double helix. Such molecules find use where it is desirable to decrease the melting temperature of hybrids, e.g. to allow for amplification with reduced melting temperatures between cycles.

The properties conferred on an oligonucleotide or polynucleotide by the presence of the analog nucleoside(s) also include an increase in hydrophobicity. The increased hydrophobicity provides for an advantage in the delivery of an oligonucleotide, particularly where delivery is across a cell membrane. Thus, in one embodiment of the invention, a method is provided for increasing the delivery of an oligonucleotide into a cell by providing for the presence of one or more nonpolar nucleosides in the oligonucleotide. Similarly, the increased hydrophobicity enhances the ability of an oligonucleotide to be presented in a lipid context, e.g. on the surface of a liposome or other lipid bilayers.

Increased hydrophobicity also provides for improvements in the isolation or purification of an oligonucleotide, e.g. by permitting the use of reverse phase HPLC in a purification procedure. A method is therefore provided for improved methods of isolation of an oligonucleotide by providing for the presence of one or more nonpolar nucleosides in the oligonucleotide.

In some embodiments of the invention, the nonpolar thymidine analog of the invention comprises an imaging or cytotoxic moiety. For purposes of imaging or cytotoxicity, the compound may be present in the form of a riboside or deoxyriboside.

Such an analog may have the a structure as set forth below:

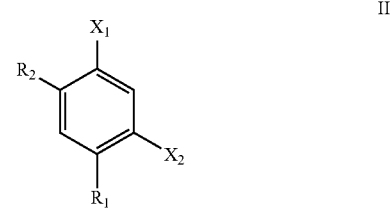

II where $R_1$ is a sugar moiety, including any pentose or hexose sugars, particularly ribose and deoxyribose, which may be in an N-glycoside or C-glycoside configuration, having a D- or L stereochemistry;

$X_1$ and $X_2$ are independently selected from I, Cl, Br, and F, with the proviso that not more than one F will be present at those positions.

$R_2$ is H, $CH_3$, an imaging or cytotoxic moiety.

For purposes of imaging or cytotoxicity, at least one imaging or cytotoxicity isotope will be present in the molecule. Such isotopes may be present as a moiety at position $R_2$, may be present as $^{11}C$ at any carbon position in the molecule, including the methyl group at position $R_2$, or may be present at $X_1$ and/or $X_2$.

An imaging moiety is usually an isotope that increases contrast between a targeted tissue, e.g. a tumor, and the surrounding non-targeted tissue in a visualization technique, e.g., radiography, positron-emission tomography, magnetic resonance imaging, direct or indirect visual inspection. Suitable imaging moieties include radiography moieties (e.g. heavy metals and radiation emitting moieties), positron emitting moieties, magnetic resonance contrast moieties, and optically visible moieties, e.g., fluorescent or visible-spectrum dyes, visible particles, etc. A cytotoxic moiety is usually a radionuclide.

Among the most commonly used positron-emitting nuclides in PET are included $^{11}C$, $^{13}N$, $^{15}O$, $^{18}F$, and $^{124}I$. Isotopes that decay by electron capture and/or γ emission are used in SPECT, and include $^{125}I$, $^{128}I$, $^{123}I$ and $^{99m}Tc$.

In some embodiments of Formula II, $R_1$ is as defined above, $R_2$ is selected from $^{11}CH_3$, $^{13}N$, $^{15}OH$, $^{18}F$, $^{123}I$, $^{124}I$, $^{125}I$, $^{128}I$, and $^{99m}Tc$, usually selected from $^{11}CH_3$, $^{18}F$, $^{123}I$, $^{124}I$, $^{125}I$, $^{128}I$, and $^{99m}Tc$; and $X_1$ and $X_2$ are independently selected from I, Cl, Br, and F.

In other embodiments of Formula II, $R_2$ is H or $CH_3$, and $X_1$ and $X_2$ are independently selected from I, Cl, Br, and F, and wherein at least one of $X_1$ and $X_2$ is $^{18}F$, $^{123}I$, $^{124}I$, $^{125}I$ or $^{128}I$.

Radiographic moieties for use as imaging moieties in the present invention include compounds and chelates with relatively large atoms, such as gold, iridium, technetium, barium, thallium, iodine, and their isotopes. It is preferred that less toxic radiographic imaging moieties, such as iodine or iodine isotopes, be utilized in the compositions and methods of the invention. Suitable radionuclides include $^{99}$Tc, $^{111}$In, and $^{67}$Ga.

Preferred magnetic resonance contrast moieties include chelates of chromium(III), manganese(II), iron(II), nickel (II), copper(II), praseodymium(III), neodymium(III), samarium(III) and ytterbium(III) ion. Because of their very strong magnetic moment, the gadolinium(III), terbium(III), dysprosium(III), holmium(III), erbium(III), and iron(III) ions are especially preferred.

Optically visible moieties for use as imaging moieties include fluorescent dyes, or visible-spectrum dyes, visible particles, and other visible labeling moieties. Fluorescent dyes such as ALEXA dyes, fluorescein, coumarin, rhodamine, bodipy Texas red, and cyanine dyes, are useful when sufficient excitation energy can be provided to the site to be inspected visually. Endoscopic visualization procedures may be more compatible with the use of such labels. Acceptable dyes include FDA-approved food dyes and colors, which are non-toxic, although pharmaceutically acceptable dyes which have been approved for internal administration are preferred.

Preferred radionuclides for use as cytotoxic moieties are radionuclides that are suitable for pharmacological administration. Such radionuclides include $^{123}$I, $^{125}$I, $^{131}$I, $^{90}$Y, $^{211}$At, $^{67}$Cu, $^{186}$Re, $^{188}$Re, $^{212}$Pb, and $^{212}$Bi. Iodine and astatine isotopes are more preferred radionuclides for use in the therapeutic compositions of the present invention, as a large body of literature has been accumulated regarding their use. $^{131}$I is particularly preferred, as are other β-radiation emitting nuclides, which have an effective range of several millimeters.

In some embodiments of Formula II, $R_1$ is as defined above, $R_2$ is selected from $^{123}$I, $^{125}$I, $^{131}$I, $^{90}$Y, $^{211}$At, $^{67}$Cu, $^{186}$Re, $^{188}$Re, $^{212}$Pb, and $^{212}$Bi, usually selected from $^{123}$I, $^{125}$I, $^{131}$I; and $X_1$ and $X_2$ are independently selected from I, Cl, Br, and F.

In other embodiments of Formula II, $R_2$ is H or $CH_3$, and $X_1$ and $X_2$ are independently selected from I, Cl, Br, and F, and wherein at least one of $X_1$ and $X_2$ is $^{123}$I, $^{125}$I, $^{131}$I.

Imaging Methods

In some embodiments, the compounds of the invention are administered for imaging use in vivo, e.g. to locate or identify sites where tumor cells are present. In these embodiments, a compound of the invention, comprising an imaging moiety, is administered to an individual (e.g., by injection, oral dosing, etc.), and labeled cells are located using standard imaging techniques, including, but not limited to, magnetic resonance imaging, computed tomography scanning, and the like.

For diagnostic in vivo imaging, the type of detection instrument is a major factor in selecting a given radionuclide. The radionuclide chosen must have a type of decay that is detectable by a given type of instrument. In general, any conventional method for visualizing diagnostic imaging can be utilized in accordance with this invention. Another important factor in selecting a radionuclide for in vivo diagnosis is that its half-life be long enough that it is still detectable at the time of maximum uptake by the target tissue, but short enough that deleterious radiation of the host is minimized.

In one embodiment, the imaging method is one of PET or SPECT, which are imaging techniques in which a radionuclide is synthetically or locally administered to a patient. The subsequent uptake of the radiotracer is measured over time and used to obtain information about the targeted tissue. Because of the high-energy (γ-ray) emissions of the specific isotopes employed and the sensitivity and sophistication of the instruments used to detect them, the two-dimensional distribution of radioactivity may be inferred from outside of the body.

Therapeutic Methods

The compounds of this invention can be incorporated into a variety of formulations for therapeutic administration. For example, the compounds may be administered to a subject having a hyperproliferative disorders, e.g., to inhibit tumor growth, to decrease inflammation associated with a lymphoproliferative disorder, to inhibit graft rejection, or neurological damage due to tissue repair, etc. Of particular interest for therapeutic purposes are anti-sense oligonucleotides; double stranded RNAi oligonucleotides; and nucleosides, which optionally comprise a cytotoxic moiety as described above. Certain nucleoside analogs are well known in the art for their ability to inhibit DNA and/or RNA replication. Such analogs have found use in the inhibition of viral replication (see, for example, U.S. Pat. Nos. 6,825,177; 6,818,633; 6,815,542; 6,809,109; 6,809,083; 6,803,371; 6,790,841, etc., herein incorporated by reference), e.g. in the treatment of herpesviruses; lentiviruses such as HIV-1; cytomegalovirus; etc. Such analogs have also found use in inhibiting the proliferation mammalian cells, including inflammatory cells such as T cells; and tumor cells. The nonpolar base analogs of the present invention may be incorporated into dideoxynucleotides and nucleosides, azido-modified nucleotides and nucleosides, etc., and administered for such purposes.

For inhibition of gene expression, antisense oligonucleotides may be used in modulating the function of nucleic acid molecules encoding a polypeptide of interest (see, for example, U.S. Pat. Nos. 6,828,151; 6,828,149; 6,825,337; etc., herein incorporated by reference), by providing antisense compounds that specifically hybridize with the mRNA of interest. The specific hybridization of an oligonucleotide compound with its target nucleic acid interferes with the normal function of the target.

The present compounds are useful for prophylactic or therapeutic purposes. As used herein, the term "treating" is used to refer to both prevention of disease, and treatment of pre-existing conditions. The prevention of proliferation is accomplished by administration of the subject compounds prior to development of overt disease, e.g., to prevent the regrowth of tumors, prevent metastatic growth, diminish restenosis associated with cardiovascular surgery, etc. Alternatively the compounds are used to treat ongoing disease, by stabilizing or improving the clinical symptoms of the patient.

The host, or patient, may be from any mammalian species, e.g., primate sp., particularly humans; rodents, including mice, rats and hamsters; rabbits; equines, bovines, canines, felines; etc. Animal models are of interest for experimental investigations, providing a model for treatment of human disease.

The susceptibility of a particular cell to treatment with the subject compounds may be determined by in vitro testing. Typically a culture of the cell is combined with a subject compound at varying concentrations for a. period of time sufficient to allow the active agents to induce cell death or inhibit migration, usually between about one hour and one week. For in vitro testing, cultured cells from a biopsy sample may be used. The viable cells left after treatment are then counted.

The dose will vary depending on the specific compound utilized, specific disorder, patient status, etc. Typically a therapeutic dose will be sufficient to substantially decrease the undesirable cell population in the targeted tissue, while maintaining patient viability. Treatment will generally be continued until there is a substantial reduction, e.g., at least about 50%, decrease in the cell burden, and may be continued until there are essentially none of the undesirable cells detected in the body.

There are many disorders associated with a dysregulation of cellular proliferation. The conditions of interest include, but are not limited to, the following conditions.

The subject compounds are useful in the treatment of a variety of conditions where there is proliferation and/or migration of smooth muscle cells, and/or inflammatory cells into the intimal layer of a vessel, resulting in restricted blood flow through that vessel, i.e., neointimal occlusive lesions. Occlusive vascular conditions of interest include atherosclerosis, graft coronary vascular disease after transplantation, vein graft stenosis, peri-anastomatic prosthetic graft stenosis, restenosis after angioplasty or stent placement, and the like.

Diseases where there is hyperproliferation and tissue remodelling or repair of reproductive tissue, e.g., uterine, testicular and ovarian carcinomas, endometriosis, squamous and glandular epithelial carcinomas of the cervix, etc. are reduced in cell number by administration of the subject compounds. The growth and proliferation of neural cells is also of interest.

Tumor cells are characterized by uncontrolled growth, invasion to surrounding tissues, and metastatic spread to distant sites. Growth and expansion requires an ability not only to proliferate, but also to down-modulate cell death (apoptosis) and activate angiogenesis to produce a tumor neovasculature.

Tumors of interest for treatment include carcinomas, e.g., colon, duodenal, prostate, breast, melanoma, ductal, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies; e.g., neuroblastoma, gliomas, etc.; hematological malignancies, e.g., childhood acute leukaemia, non-Hodgkin's lymphomas, chronic lymphocytic leukaemia, malignant cutaneous T-cells, mycosis fungoides, non-MF cutaneous T-cell—lymphoma, lymphomatoid papulosis, T-cell rich cutaneous lymphoid hyperplasia, bullous pemphigoid, discoid lupus erythematosus, lichen planus, etc.; and the like.

Other hyperproliferative diseases of interest relate to epidermal hyperproliferation, tissue, remodeling and repair. For example, the chronic skin inflammation of psoriasis is associated with hyperplastic epidermal keratinocytes as well as infiltrating mononuclear cells, including CD4+ memory T cells, neutrophils and macrophages.

The proliferation of immune cells is associated with a number of autoimmune and lymphoproliferative disorders. Diseases of interest include multiple sclerosis, rheumatoid arthritis and insulin dependent diabetes mellitus. Evidence suggests that abnormalities in apoptosis play a part in the pathogenesis of systemic lupus erythematosus (SLE). Other lymphoproliferative conditions the inherited disorder of lymphocyte apoptosis, which is an autoimmune lymphoproliferative syndrome, as well as a number of leukemias and lymphomas. Symptoms of allergies to environmental and food agents, as well as inflammatory bowel disease, may also be alleviated by the compounds of the invention.

Formulations

The compounds of this invention can be incorporated into a variety of formulations for therapeutic administration. More particularly, the compounds of the present invention can be formulated into pharmaceutical compositions by combination with appropriate pharmaceutically acceptable carriers or diluents, and may be formulated into preparations in solid, semi-solid, liquid or gaseous forms, such as tablets, capsules, powders, granules, ointments, solutions, suppositories, injections, inhalants, gels, microspheres, and aerosols. As such, administration of the compounds can be achieved in various ways, including oral, buccal, rectal, parenteral, intraperitoneal, intradermal, transdermal, intracheal, etc., administration. The active agent may be systemic after administration or may be localized by the use of regional administration, intramural administration, or use of an implant that acts to retain the active dose at the site of implantation.

In pharmaceutical dosage forms, the compounds may be administered in the form of their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

The compounds can be formulated into preparations for injections by dissolving, suspending or emulsifying them in an aqueous or nonaqueous solvent, such as vegetable or other similar oils, synthetic aliphatic acid glycerides, esters of higher aliphatic acids or propylene glycol; and if desired, with conventional, additives such as solubilizers, isotonic agents, suspending agents, emulsifying agents, stabilizers and preservatives.

The term "unit dosage form", as used herein, refers to physically discrete units suitable as unitary dosages for human and animal subjects, each unit containing a predetermined quantity of compounds of the present invention calculated in an amount sufficient to produce the desired effect in association with a pharmaceutically acceptable diluent, carrier or vehicle. The specifications for the novel unit dosage forms of the present invention depend on the particular compound employed and the effect to, be achieved, and the pharmacodynamics associated with each compound in the host.

The pharmaceutically acceptable excipients, such as vehicles, adjuvants, carriers or diluents, are readily available to the public. Moreover, pharmaceutically acceptable auxiliary substances, such as pH adjusting and buffering agents, tonicity adjusting agents, stabilizers, wetting agents and the like, are readily available to the public.

A typical dosage may be a solution suitable for intravenous administration; a tablet taken from two to six times daily, or one time-release capsule or tablet taken once a day and containing a proportionally higher content of active ingredient, etc. The time-release effect may be obtained by capsule materials that dissolve at different pH values, by capsules that release slowly by osmotic pressure, or by any other known means of controlled release.

Those of skill will readily appreciate that dose levels can vary as a function of the specific compound, the severity of the symptoms and the susceptibility of the subject to side effects. Some of the specific compounds are more potent than others. Preferred dosages for a given compound are readily determinable by those of skill in the art by a variety of means. A preferred means is to measure the physiological potency of a given compound.

Kits

Also provided are kits for practicing the subject methods. The kits according to the present invention may comprise: (a) at least one nucleoside or nucleotide analog of the invention, and may further comprise enzymes, buffers, primers, and the like for performing polymerization reactions; and (b) instructions for using the provided modified nucleoside or nucleotide. Such analogs may be provided lyophilized, in solution, etc.

Kits may also be provided for use in the synthesis of oligonucleotides comprising nonpolar base analogs. Such kits may comprise modified H-phosphonate or phosphoroamidite derivatives to introduce nonpolar base analogs into a polynucleotide. The kits may further comprise additional reagents which are required for or convenient and/or desirable to include in the reaction mixture prepared during the subject methods, where such reagents include phosphoroamidite reagents and buffers for DNA synthesis; columns.

The various reagent components of the kits may be present in separate containers, or may all be precombined into a reagent mixture for combination with samples. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

Experimental

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the scope of the invention.

EXAMPLE 1

To probe steric effects in a systematic way, it is desirable to have a set of molecules of gradually increasing size, to act as "molecular rulers" for active site size and deformability. Here we describe the preparation and structures of such a series of compounds. We took thymidine as a starting point, and designed a set of compounds with smaller (the dihydrogen case, 1) or increasingly larger substituents (dihalogen deoxyribosides 2-5). Computer models suggested that progression from hydrogen and moving down the halogen series would produce bond lengths at the 2,4 positions (corresponding to oxygens of thymidine, 6) ranging from 1.1 to 2.0 Å (FIG. 1). Group radii also would increase gradually along the series as well.

We adopted a generalized strategy for preparing the first four of the five C-glycosides. Our approach involved reactions of a selectively lithiated dihalotoluenes or toluene itself in the case of 1 with the known deoxyribonolactone derivative utilized by Woski. In practice, the lithiated arenes reacted moderately well with the lactone, yielding the C-glycosides with yields ranging from 29% (for 4) to 35% (for 5). The acidic H3 between two fluorides of 2a hampered the lithiation at Br position, so we modified the lithiation step to Grignard for 2b. In the four coupling reactions the desired beta isomer was the major product; the minor alpha isomers were obtained in yields less than 10%. The desired compounds were easily separated by silica gel column and the beta orientation was confirmed by NOE measurements involving the 2' protons and their vicinal neighbors. Deprotection of the siloxane 3',5' protecting group was carried out smoothly with tetrabutylammonium fluoride, giving the first four compounds of the series in yields of 90-97%. The 2,4-substitutions were confirmed (relative to other possible isomers) by HMBC and NOE measurements, and mass spectra confirmed that the 2,4-halogens in 2-4 remained intact.

The diiodide 5 required a different approach, and was constructed from the dibromonucleoside 4. To avoid the problem of selective lithiation in the presence of two other iodo groups, we prepared this final compound (the largest of the series) by replacing the bromo groups of deoxynucleoside 4 with iodines using the copper-catalyzed strategy described by Buchwald. Although the procedure had not been previously described for multiple bromo groups, we applied it with modest success in this case yielding the diiodide in 22% yield.

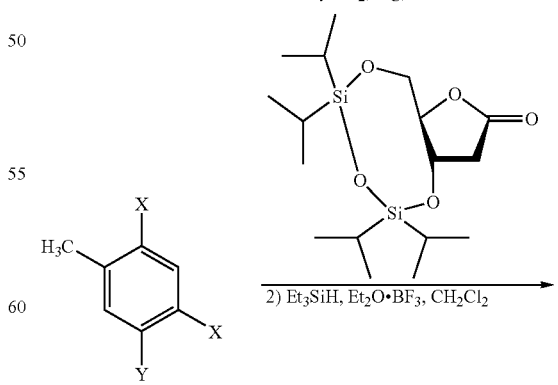

Scheme 1

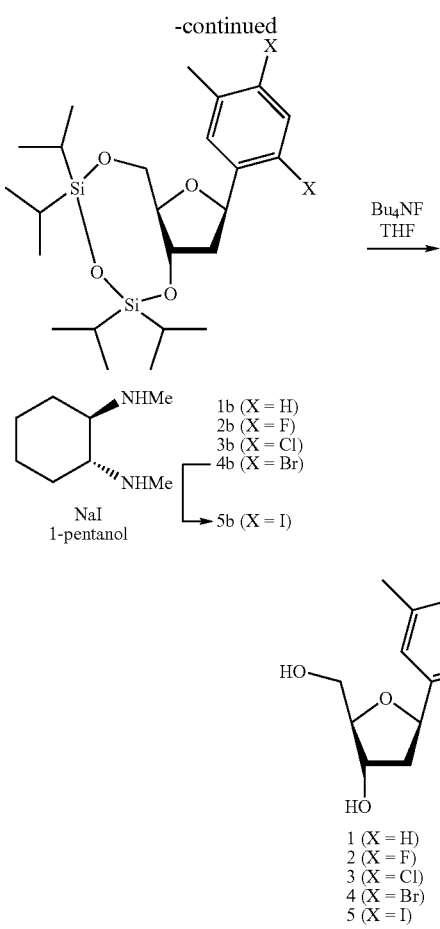

1b (X = H)
2b (X = F)
3b (X = Cl)
4b (X = Br)
5b (X = I)

1 (X = H)
2 (X = F)
3 (X = Cl)
4 (X = Br)
5 (X = I)

PM3 calculations of the aryl substituents of this series were used to estimate bond lengths of the base mimics. Of particular interest are the bond lengths of the varied 2,4 substituents, which vary over a 2.0 Å range (FIG. 1). Maps of the electrostatic charges over the van der Waals surfaces are also shown for comparison (FIG. 1). Overall, the new dichloro, dibromo, and diiodo compounds appear to have quite low polarity. The surface potentials vary by a relatively small amount, but they suggest that the three largest cases have negative charge density at the center of the ring similar to that of the dihydrogen case, with a small increase for the largest case (the diiodide). Only the difluoro case has less negative charge density, presumably because of the high electronegativity of fluorine. Overall, the shapes are similar to that of the parent thymine.

Figure 2:
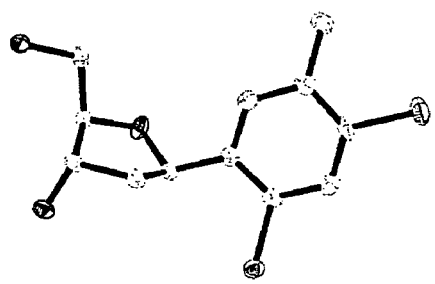
FIG. 2A-2B. Solid-state X-ray crystal structure of dichlorotoluene deoxyglycoside 3. A) ORTEP drawing of 3, showing β-anomeric configuration, C-3'-exo (S type) conformation of deoxyribose, and anti glycosidic orientation. B) Comparison of dihedral angles in the solid-state structures of 3, 2, and thymidine (6).

We were able to obtain crystals of the dichlorotoluene deoxyribose derivative from chloroform, which afforded a solid-state X-ray structure (FIG. 2A). The structure shows a C2'-exo sugar conformation, falling into the "S" family of conformers, and an anti glycosidic orientation is present. Comparison of this structure to that of the difluorotoluene analogue shows a similar structure and conformation (FIG. 2B). The C—Cl bond lengths in the crystal structure are 1.74 and 1.75 Å, which is, of course, substantially longer than the corresponding C—F bonds in the difluoroluene deoxyriboside crystal structure (1.34 Å) (FIG. 1B). Overall, then, the dichloro analogue adopts a structure nearly the same as the reported crystal structure of thymidine.

Because crystal packing forces may alter conformations in relatively flexible five-membered rings, the structures of these isosteres in solution were of greater interest than the solid-state structures. We carried out an analysis of ring coupling constants to assign deoxyribose conformations for the series of five compounds. The data are shown in Table 1. All five compounds are quite similar, and all are assigned as "S"-type sugars. Thus the conformations falls into a relatively narrow range, and this range is not greatly different from the conformational preference of thymidine itself (which is reported as 70% S). We conclude that varying bonds lengths (at the 2-position on the benzene ring in particular) does not markedly affect the ring conformation.

We also examined bond rotameric preferences for the glycosidic bonds, which was evaluated by NOE experiments focused on the C-1' proton. A syn glycoside generally shows large NOE enhancements at the 6-position of the "nucleobase" due to the proximity of these two protons. However, natural thymidine shows only a small enhancement due to its relatively strong anti orientational preference, and our experiments showed similarly small NOEs to the C6-protons of the four dihalo compounds in this series.

TABLE 1

Nucleoside conformations for 1-5 determined by $^1$H-NMR measurements in $D_2O$.

| | coupling constants | | | | | |
|---|---|---|---|---|---|---|
| | H1'-H2' | H1'-H2" | H2'-H3' | H2"-H3' | | |
| 1 | 10.68 | 5.49 | 5.92 | 1.68 | 2.24 | 13.71 |
| 2[bb] | 10.37 | 5.80 | 5.79 | ≈1.0 | 2.44 | 13.58 |
| 3 | 10.26 | 5.62 | 6.01 | 1.85 | 2.18 | 13.70 |
| 4 | 10.23 | 5.76 | 6.08 | 1.95 | 2.47 | 13.76 |
| 5 | 10.14 | 5.73 | 5.75 | 1.53 | 2.33 | 13.59 |
| | summed J values[a] | | | | | |
| | Σ1' | Σ2' | Σ2' | Σ3' | | |
| 1 | 16.17 | 30.31 | 20.88 | 9.84 | | |
| 2[b] | 16.17 | 29.74 | 20.88 | 9.73 | | |
| 3 | 15.88 | 29.97 | 21.17 | 10.04 | | |
| 4 | 15.99 | 30.07 | 21.47 | 10.50 | | |
| 5 | 15.87 | 29.48 | 20.85 | 9.61 | | |

[a]Σ1' = J1'2' + J1'2"; Σ2' = J1'2' + J2'3' + J2'2"; Σ2' = J1'2" + J2"3' + J2'2"; Σ3' = J2'3' + J2"3' + J3'4'.

Overall, the results show that this new series of five compounds is readily prepared, and that all five adopt conformations very close to that of thymidine. Thus these nucleoside analogues are broadly useful as steric probes of enzyme active sites that normally process thymidine nucleosides or nucleotides. In addition, when incorporated into DNA they are useful as steric probes of protein-DNA recognition in general.

EXAMPLE 2

Since steric effects are widely believed to be crucial to biological selectivity in enzymatic systems, it would be useful to have chemical tools to probe such effects in a systematic way. With this in mind we conceived of a new series of thymine analogues; 2,4-diHydrogentoluene (H), difluorotoluene (F), 2,4-dichlorotoluene (L), 2,4-dibromotoluene (B), and 2,4-diiodotoluene (I) in which the size is varied systematically by replacing the oxygen nucleobase substituents with hydrogen, fluorine, chlorine, bromine, and iodine (FIG. 1). Since the oxygens are the main protruding groups of thymine on its Watson-Crick edge, this replacement has the effect of maintaining an approximate shape of T while gradually increasing size by about one Angstrom across the series. Here we describe the derivatization of these compounds for incorporation into oligonucleotides, the characterization of DNA strands containing them, and the evaluation of their pairing and stacking properties in the double helix.

Synthesis of Modified Nucleoside Phosphoramidites. The C-glycoside series (dH, dL, dB, dI) was prepared as described below, while one compound (dF) is now commercially available as the phosphoramidite derivative. 5'-tritylation of the other four compounds was carried out in pyridine in the presence of N,N-diisopropylethylamine, giving the corresponding 5'-ethers (1a-4a) in yields of 45-51%. The 3'-phosphoramidite species were prepared using standard methods, yielding the desired phosphorylated species (1b-4b) in 50-74% (Scheme 2).

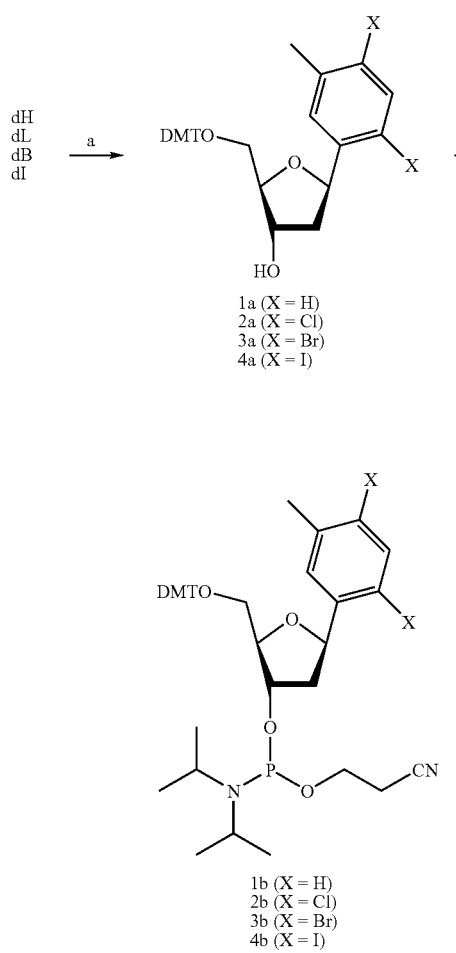

Conditions: (a) 4,4'-dimethoxytrityl chloride, DIPEA, pyridine; (b) 2-cyanoethyl N, N-diisopropylchlorophosphoramidite, DIPEA, CH2Cl2.

Oligodeoxynucleotide Synthesis. Phosphoramidite derivatives we prepared as described above. The phosphoramidite derivative of analogue dF was purchased from Glen Research. DNA oligonucleotides were synthesized on an Applied Biosystems 394 synthesizer using standard β-cyanoethylphosphor-amidite chemistry. Self-complementary oligomers with 5'-dangling ends (X) were synthesized in DMT-off mode and purified by reverse phase HPLC (SB-C18 column, 0 to n%, 30 min gradient $CH_3CN$/50 mM triethylammonium acetate (TEAA) (pH 7.5), n=18, 20, 25, 28, 33, 37, 40 for X=none, T, H, F, L, B, I). Oligomers for base pairing were synthesized in DMT-on mode. Sequences containing only natural bases were purified by Poly-Pack™ II (Glen Research, cat. no. 60-3100-10) and the sequences with a nonnatural base were purified by reverse phase HPLC (SB-C18 column, 0 to 50%, 20 min gradient $CH_3CN$/50 mM TEM (pH 7.5)). The post-HPLC detritylation and precipitation followed the standard protocol. All oligonucleotides with a nonnatural base were characterized by MALDI mass spectrometry and their purities were checked by analytical reverse phase HPLC.

The oligomers were quantitated by absorbance at 260 nm. Molar extinction coefficients were calculated by the nearest neighbor method. Values for oligonucleotides containing nonnatural residues were obtained in the following way: The molar extinction coefficients for each of the new nucleosides were measured at 260 nm in methanol because of their low water solubility. The molar extinction coefficients for dH, dF, dL, dB, and dI were found to be 250, 1000, 250, 500, and 3900 $M^{-1}cm^{-1}$, respectively. The individual extinction coefficients for all the bases in a given oligomer were summed. Since in the most cases the content of nonnatural residues in the sequences is low, this estimation method is unlikely to generate large errors in concentration.

Thermal Denaturation Studies. After the samples were prepared in melting buffer (1M NaCl, 10 mM phosphate buffer (pH 7.0) with 0.1 mM EDTA), they were heated to 95° C. and allowed to slowly cool at a rate of 1° C./min to 5° C. The melting studies were carried out in Teflon-stoppered 1 cm path length quartz cells on a Varian Cary 1 UV-vis spectophotometer equipped with thermoprogrammer. Absorbance was monitored at 280 nm for stacking and at 260 nm for base pairing. In all cases the complexes displayed sharp, apparently two-state transitions. The data were analyzed by the melt curve processing program, MeltWin v. 3.0. Melting temperatures ($T_m$) were determined by computer-fit of the first derivative of absorbance with respect to 1/T. Uncertainty in $T_m$ is estimated at ±0.5° C. based on repetitions of experiments. Free-energy values were derived by two methods: (1) computer-fitting the denaturation data with an algorithm employing linear sloping baselines, using the two-state approximation for melting. Fits were excellent, with $\chi^{-2}$ values of $10^{-6}$ or better. (2) Van't Hoff thermodynamic parameters were derived from linear plots of $1/T_m$ vs $\ln[C_T]$ by measuring $T_m$ as a function of concentration. Close agreement was seen with the results from curve-fitting, indicating that the two-state approximation is a reasonable one for these two sequences.

Results

Sequence Design. We incorporated all five phosphoramidites into three new sequence contexts each for further study of pairing and stacking properties. The first is a self-complementary sequence designed to form a hexamer duplex, with the nonnatural base analogue overhanging (dangling) at the 5' ends (Table 2). This same sequence context has been used previously in several studies of DNA base stacking. The second and third contexts comprise a pair of 12mer sequences that form duplexes with well-behaved two-state behavior. One strand is pyrimidine-rich, while the other is purine-rich; we substituted each analogue at a central position of each strand to test two widely varied sequence contexts for pairing effects.

Base Stacking. DNA base stacking stability has been correlated with the size of compounds when mono-, bi-, tri-, and tetra-cyclic base analogues were compared. To test this with the present series, which varies in size by a smaller amount, we examined the short self-complementary oligonucleotides by thermal denaturation experiments. The self-complementary duplexes contained the modified nucleosides as a 5' overhanging base. The data are given in Table 2. The results show that all five compounds stabilized the duplex more than natural thymidine does in the same position. The least stabilizing of the series was the smallest, the toluene case (H). Interestingly, the remaining four larger compounds (F, L, B, I) showed only small differences in their stabilization of this duplex, with a small increase in stabilization with the increase in size overall.

Because stacking propensities of DNA bases and analogues have been most strongly correlated with surface area and hydrophobicity, we calculated these parameters for the base analogues and their deoxyriboside derivatives. Results showed that the surface area of the base analogues increased in a regular way from 154 to 201 Å2 as the series proceeded from the smallest substituents (H) to the largest (I). Calculated log P (octanol-water) values were determined for the free deoxyribosides of the series; these also increased monotonically as size increased. The smallest log P value (for dH) was 1.25, and the largest (for dI) was 3.97. Thus these nucleosides are expected to be strongly hydrophobic compared to thymidine nucleoside (calculated log P=−1.29), which is a relatively polar, water-soluble compound.

Figure 3:
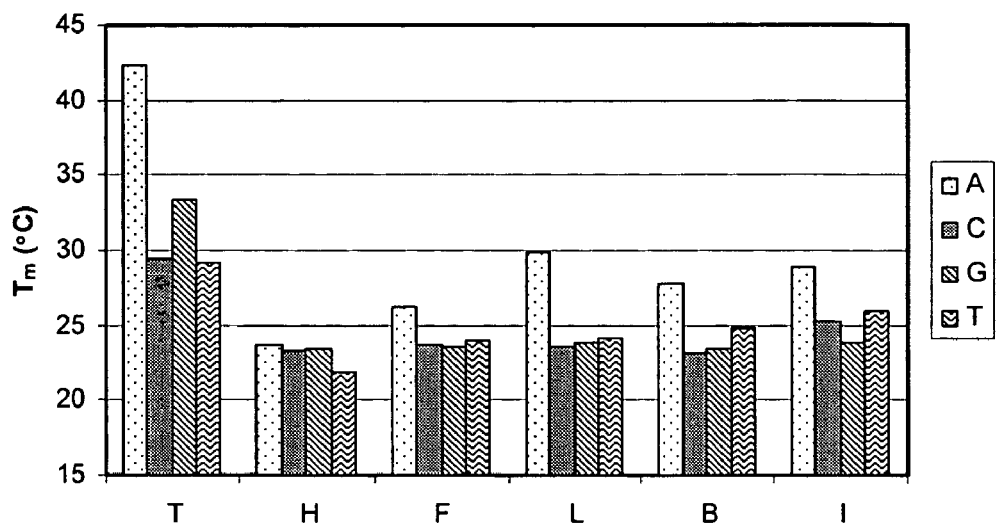
FIG. 3A-3B. Base pairing of nonpolar thymine analogues (H, F, L, B, I) opposite the natural bases in the center of a 12-base pair duplex, evaluated by thermal melting temperature ($T_m$). Nonnatural base analogues were substituted in a pyrimidine-rich strand (A) or a purine-rich strand (B).
Figure 3:
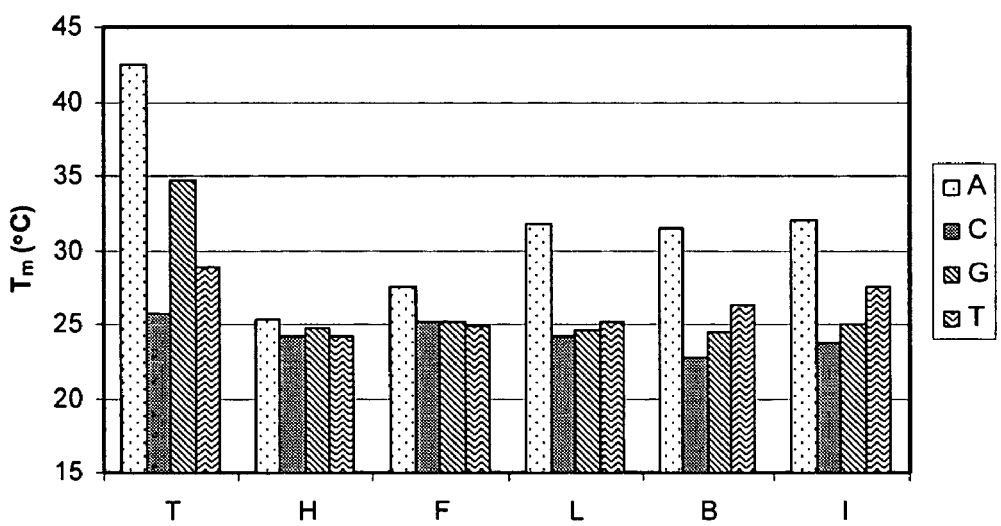

Base Pairing. Pairing studies of the nonpolar series were then carried out in a twelve base pair duplex; results are summarized in FIG. 3. The data showed that all five compounds are quite destabilizing (compared to T) when paired opposite natural bases. Results were the same regardless of whether the analogues were in the pyrimidine- or purine-rich strand (FIGS. 3A and 2B). For each analogue, pairing stability was nearly the same regardless of which natural base was opposite it; however, all five compounds showed a small but significant preference for adenine as partner. The data also showed that, although all analogues were destabilizing opposite the natural bases, there was a general lessening of the destabilization as the analogue increased in size. Of the five nonpolar compounds, the diiodo case was the least destabilizing when paired opposite natural bases.

Figure 4:
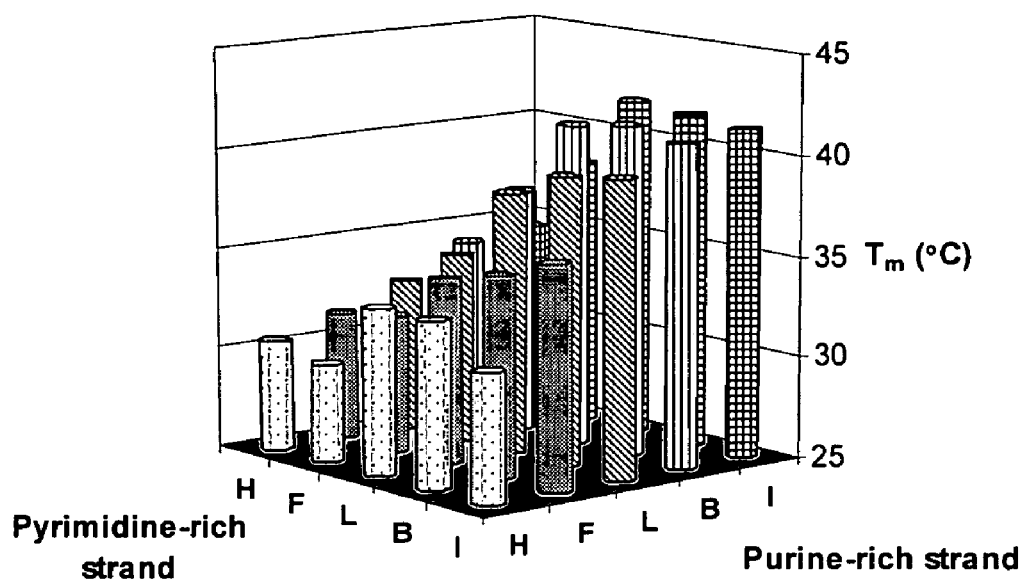
FIG. 4. The pairing of hydrophobic nucleosides with themselves near the center of a 12-base pair duplex, as measured by thermal melting temperature.

Finally, the entire set of nonnatural pairs was tested, evaluating various combinations of compounds (H, F, L, B, I) paired against each other. The data showed a wide range of thermal stabilities for the duplexes containing nonpolar pairs (FIG. 4). Most of the nonnatural pairs were destabilizing relative to a T-A base pair in the same context; the most destabilizing nonpolar pairs involved the smallest base analogues. The H-H and F-H pairs were among these (FIG. 3). Notably, however, some pairs, involving L, B, I in the pyrimidine strand and B, I in the purine strand, were not as destabilizing, and a few (L-I, B-I and I-I in particular) were equally as stabilizing as a thymine-adenine pair in this context.

A more detailed evaluation of the thermodynamics of duplexes containing the smaller set of self-pairs was carried out by combined use of melt curve fitting and van't Hoff analysis (Table 3). The data revealed the I-I self-pair to be the most stable, and the H-H pair to be the least stable, with a large difference of 13° C. in $T_m$ and 2.7 kcal/mol between these dodecamer duplexes containing only a single pair difference. Both the $T_m$ and free energy values for the I-I-containing duplex were identical to the values for the same duplex containing a T-A pair at that site.

TABLE 2

Thermodynamic parameters for stacking for thymine and nonpolar thymine analogs, as measured by dangling end thermal denaturation studies with self-complementary strands (5'-XCGCGCG)[a].

| Dangling residue (X) | $T_m$ (° C.)[b] | $\Delta T_m$ (° C.) | $\Delta H°$ (kcal/mol, van't Hoff) | $\Delta S°$ (cal/K · mol, van't Hoff) | $\Delta G°_{37}$ (kcal/mol, van't Hoff) | $\Delta G°_{37}$ (kcal/mol, fits) | $\Delta\Delta G°$ stacking per base (kcal/mol) |
|---|---|---|---|---|---|---|---|
| none | 38.6 | — | −41.6 ± 5.0 | −109 ± 16 | −7.8 ± 0.2 | −7.8 ± 0.1 | — |
| T | 46.0 | 7.4 | −54.4 ± 4.1 | −146 ± 13 | −9.1 ± 0.1 | −9.1 ± 0.1 | 0.65 |
| H | 49.7 | 11.1 | −55.4 ± 2.0 | −147 ± 6 | −9.7 ± 0.1 | −9.7 ± 0.0 | 0.95 |
| F | 52.4 | 13.8 | −54.5 ± 0.9 | −143 ± 3 | −10.1 ± 0.0 | −10.1 ± 0.0 | 1.15 |
| L | 52.3 | 13.7 | −52.7 ± 1.2 | −138 ± 4 | −10.0 ± 0.1 | −10.1 ± 0.0 | 1.10 |
| B | 54.3 | 15.7 | −62.0 ± 2.1 | −165 ± 7 | −10.8 ± 0.1 | −10.2 ± 0.0 | 1.50 |
| I | 53.8 | 15.2 | −55.7 ± 4.4 | −146 ± 14 | −10.4 ± 0.2 | −10.2 ± 0.1 | 1.30 |

[a]Conditions: 1M NaCl, 10 mM phosphate buffer (pH 7.0) with 0.1 mM EDTA, monitored at 280 nm.
[b]5.0 μM DNA strand concentration for $T_m$ value shown.

TABLE 3

Stabilities of X-X self-pairs of nonpolar thymidine analogues (H, F, L, B, I),
as measured by melting temperature ($T_m$) and free energy ($\Delta G°$) for the duplexes.[a]

| 5'-CTTTTCXTTCTT<br>3'-GAAAAGXAAGAA<br>[SEQ ID NO:3] | $T_m$ (° C.)[b] | $\Delta H°$ (kcal/mol, van't Hoff) | $\Delta S°$ (cal/K · mol, van't Hoff) | $\Delta G°_{37}$ (kcal/mol, van't Hoff) | $-\Delta G°_{37}$ (kcal/mol, fits) |
|---|---|---|---|---|---|
| H · H | 29.4 | −54.3 ± 4.6 | −152 ± 15 | −7.1 ± 0.1 | −7.0 ± 0.1 |
| F · F | 31.9 | −65.4 ± 7.8 | −187 ± 26 | −7.2 ± 0.2 | −7.3 ± 0.1 |
| L · L | 38.0 | −73.3 ± 11.2 | −208 ± 36 | −8.5 ± 0.3 | −8.5 ± 0.1 |
| B · B | 40.8 | −73.0 ± 3.5 | −205 ± 11 | −9.3 ± 0.1 | −9.3 ± 0.1 |
| I · I | 42.1 | −69.0 ± 3.5 | −192 ± 6 | −9.5 ± 0.0 | −9.7 ± 0.1 |

[a]Conditions: 1M NaCl, 10 mM phosphate buffer (pH 7.0) with 0.1 mM EDTA, monitored at 260 nm.
[b]2.6 □M concentration for each DNA strand for $T_m$ value. For reference, $T_m$ = 42.4° C. for $X_1$ = T, $X_2$ = A and $T_m$ = 42.4° C. for $X_1$ = A, $X_2$ = T.

Since these nonpolar analogues lack the ability to undergo Watson-Crick hydrogen bonding, their stabilization of DNA (in cases where stabilization does occur) must arise instead from favorable stacking and/or the associated changes in solvation. The current data show that the halogenated compounds increase in their stacking ability by a small amount as size increases, a trend that is generally expected since surface area and hydrophobicity—which are strong predictors of stacking in DNA—increase as well. However, since the size change is relatively small across the series, the difference in stacking is moderate. A similar magnitude of stacking across the series is probably a desirable property for a number of biophysical and mechanistic applications, such as probing protein-DNA interactions and enzyme active sites. This keeps non-steric properties as equal as possible as the effects of these compounds are compared, allowing for more confident conclusions about steric influences alone.

With natural bases as partners, the members of this series behaved remarkably similarly in pairing ability despite the changes in size. Stability was nearly the same regardless of which natural base was opposite the compounds. It is interesting, however, that all five compounds showed a small but significant preference for adenine as partner. We attribute this to two known properties of adenine: first, it is the strongest stacking of the four natural bases. Probably for the same reason, adenine is known to be the most stabilizing of the natural bases when the partner lacks a base altogether (an abasic site). The second property is the relatively weak salvation of adenine compared to the other three bases. If a nonpolar base is placed opposite adenine, partially desolvating it, this would have less energetic cost than if any other base were desolvated. Looking at the trend in the series, there was a slightly more pronounced preference for adenine exhibited by the largest members of the series. One possible explanation for this is the greater hydrophobicity of the larger analogues, which might lead to a stronger preference for the least well solvated natural base.

The earliest studies of nonpolar-nonpolar base analogue pairs reported that nonpolar-nonpolar pairs were less destabilizing than pairs of nonpolar bases opposite the polar natural bases, and this same effect is observed here as well. This selective pairing of nonpolar compounds can be attributed to avoidance of desolvation costs when pairing opposite polar compounds, as well as to increased surface area of hydrophobic contact. Notably, some of the pairs in this series are not destabilizing to DNA, and a few of the largest pairs, such as B-I and I-I, were as stabilizing as a natural base pair. Thus these last pairs can be added to a small but growing list of nonpolar aromatic DNA base replacements that are stable and selective in DNA, but which are also orthogonal, pairing poorly with natural bases. Such properties may one day find use in designed genetic pairing systems.

Materials and Methods

General Procedure for preparation of 5'-O-tritylated β-C-Nucleosides. The free nucleoside (0.5 mmol) was coevaporated with dry pyridine twice and dissolved in pyridine (3 mL). To the solution were added diisopropylethylamine (0.13 mL, 1.5 equiv) and 4,4'-dimethoxytrityl (DMT) chloride (170 mg, 1.0 equiv). The mixture was stirred at room temperature for 2 h and then an additional portion of DMTCl (42 mg, 0.25 equiv) was added to the solution. After 1 h, the reaction mixture was quenched with methanol (5 mL) and volatiles were removed in vacuo. The residue was loaded onto a silica gel column (pre-equilibrated with 5% triethylamine in hexane) and eluted (30:10:1, hexane:ethylacetate:triethylamine).

General Procedure for preparation of 3'-O-Phosphoramidites. The 5'-O-tritylated β-C-nucleoside (0.4 mmol) was dissolved in dry dichloromethane (5 mL), and to this were added diisopropylethylamine (0.28 mL, 4 equiv) and 2-cyanoethyl N,N-diisopropylchlorophosphoramidite (0.13 mL, 1.5 equiv). The reaction mixture was stirred at room temperature for 3 h, then all volatiles were removed in vacuo. The residue was loaded onto a silica gel column (pre-equilibrated with 5% triethylamine in hexane) and eluted (60:20:1, hexane:ethylacetate:triethylamine).

1',2'-Dideoxy-β-1'-(3-methylphenyl)-5'-O-(4,4'-dimethoxytrityl)-D-ribofuranose (1a). $^1$H NMR (CDCl$_3$, ppm) 7.47 (d, 2H, J=7.2 Hz), 7.36 (dd, 4H, J=8.8, 2.4 Hz), 7.29-7.15 (m, 6H), 7.08 (d, 1H, J=7.2 Hz), 6.82 (d, 4H, J=8.8 Hz), 5.14 (dd, 1H, J=10, 5.6 Hz), 4.42 (br, 1H), 4.07-4.04 (m, 1H), 3.78 (s, 6H), 3.37-3.34 (m, 1H), 3.29-3.25 (m, 1H), 2.30 (s, 3H), 2.23 (ddd, 1H, J=13, 5.6, 2.0 Hz), 2.10-2.03 (m, 1H); $^{13}$C NMR (CDCl$_3$, ppm) 158.6, 145.1, 141.96, 138.2, 136.3, 130.3, 128.4, 128.1, 127.0, 126.9, 123.4, 113.3, 86.5, 86.4, 80.3, 74.9, 64.7, 55.4, 44.1, 21.7; HRMS (FAB+, NBA matrix) calcd mass 533.2303 for [C$_{33}$H$_{34}$O$_5$+Na]. Found 533.2288.

1',2'-Dideoxy-β-1'-(3-methylphenyl)-5'-O-(4,4'-dimethoxytrityl)-D-ribofuranose cyanoethyl N,N-diisopropylphosphoramidite (1b). $^1$H NMR (CDCl$_3$, ppm) 7.50-7.47 (m, 2H), 7.39-7.35 (m, 4H), 7.28-7.18 (m, 6H), 7.09-7.07 (m, 1H), 6.82-6.79 (m, 4H), 5.13 (app quintet, 1H, J=6.0 Hz), 4.53-4.50 (m, 1H), 4.23 (br, 1H), 3.85-3.66 (m, 2H), 3.78 (app d, 6H, J=3.0 Hz, OCH$_3$), 3.63-3.58 (m, 2H), 3.35-3.29 (m, 1H), 3.26-3.22 (m, 1H), 2.61 (app t, 1H, J=6.5 Hz), 2.45 (app t+d, 1H, J=7.0 (for triplet), 2.0 (for doublet) Hz), 2.41-2.31 (m, 1H), 2.31 (s, 3H, ArCH$_3$), 2.08-2.01 (m, 1H), 1.20-1.15 (m, 8H), 1.08 (app d, 4H, J=6.5 Hz); $^{13}$C NMR (CDCl$_3$, ppm) 158.7, 145.2, 141.9, 138.2 (d), 136.4 (m), 130.4 (d), 128.6 (d), 128.0, 127.0 (t), 123.5, 117.8 (d), 113.3, 86.3 (d), 85.9 (d), 80.6 (d), 76.5 (d), 76.2 (d), 64.5 (d), 58.6 (d), 55.5 (d), 43.5 (m), 31.9, 24.8 (m), 22.9, 21.7, 20.6 (m), 14.4; HRMS (FAB+, NBA matrix) calcd mass 733.3382 for [C$_{42}$H$_{51}$N$_2$O$_6$P+Na]. Found 733.3378.

1',2'-Dideoxy-β-1'-(2,4-dichloro-5-methylphenyl)-5'-O-(4,4'-dimethoxytrityl)-D-ribofuranose (2a). $^1$H NMR (CDCl$_3$, ppm) 7.54 (s, 1H), 7.46 (d, 2H, J=8.0 Hz), 7.36-7.33 (m, 4H), 7.30-7.20 (m, 4H), 6.83 (dd, 4H, J=9.0, 1.5 Hz), 5.41 (dd, 1H, J=10, 6 Hz), 4.41-4.39 (m, 1H), 4.07-4.05 (m, 1H), 3.79 (s, 6H), 3.37 (app d, 2H, J=4.5 Hz), 2.46 (ddd, 1H, J=14, 6.0, 5.0 Hz), 2.22 (s, 3H), 2.04-1.87 (m, 1H); $^{13}$C NMR (CDCl$_3$, ppm) 158.4, 144.7, 138.4, 135.9, 134.9, 133.3, 130.0, 129.0, 128.6, 128.1, 127.8, 126.8, 113.1, 86.3, 85.8, 76.4, 74.4, 64.1, 55.2, 42.4, 19.5; HRMS (FAB+, NBA matrix) calcd mass 601.1524 for [C$_{33}$H$_{32}$Cl$_2$O$_5$]. Found 601.1553.

1',2'-Dideoxy-β-1'-(2,4-dichloro-5-methylphenyl)-5'-O-(4,4'-dimethoxytrityl)-D-ribofuranose cyanoethyl N,N-diisopropylphosphoramidite (2b). $^1$H NMR (CDCl$_3$, ppm) 7.62 (app d, 1H, J=9.5 Hz), 7.49-7.46 (m, 2H), 7.38-7.32 (m, 4H), 7.29-7.25 (m, 2H), 7.23-7.19 (m, 2H), 6.84-6.80 (m, 4H), 5.40 (app quintet, 1H, J=5 Hz, H1'), 4.52-4.45 (m, 1H, H3'), 4.21 (br, 1H, H4'), 3.85-3.75 (m, 1H), 3.78 (app d, 6H, J=3.5 Hz, OCH$_3$), 3.68-3.54 (m, 3H), 3.40 (app ddd, 1H, J=22.10, 3.9 Hz, H5'), 3.27 (app t+d, 1H, J=10.6 (for triplet), 3.7 (for doublet) Hz, H5'), 2.61 (app t, 1H, J=6.0 Hz), 2.63-2.51 (m, 1H, H2'), 2.44 (app t, 1H, J=6.5 Hz), 2.22 (app d, 3H, J=5.0 Hz, ArCH$_3$) 1.90-1.83 (m, 1H, H2'), 1.18-1.15 (m, 8H), 1.06 (app d, 4H, J=6.5 Hz); $^{13}$C NMR (CDCl$_3$, ppm) 158.7, 145.1 (d), 138.6 (d), 136.3 (m), 135.3, 133.6, 130.4 (d), 129.3 (d), 129.6 (d), 128.5 (d), 128.1, 127.1 (d), 117.8 (d), 113.4, 86.5, 85.8 (d), 76.0 (t), 64.0 (d), 58.6 (t), 55.5 (d), 43.5 (t), 42.1, 31.9, 24.8 (m), 22.9, 20.6 (d), 20.4 (d), 19.9, 14.4; HRMS (FAB+, NBA matrix) calcd mass 801.2602 for [C$_{42}$H$_{49}$Cl$_2$N$_2$O$_6$P]. Found 801.2600.

1',2'-Dideoxy-β-1'-(2,4-dibromo-5-methylphenyl)-5'-O-(4,4'-dimethoxytrityl)-D-ribofuranose (3a). $^1$H NMR (CDCl$_3$, ppm) 7.80 (s, 1H), 7.47 (d, 2H, J=7.0 Hz), 7.38-7.35 (m, 4H), 7.30 (app t, 2H, J=8.0 Hz), 7.21 (app t, 2H, J=7.0 Hz), 6.85 (d, 4H, J=9.0 Hz), 5.33 (dd, 1H, J=9.5, 6.0 Hz), 4.37-4.34 (m, 1H), 4.06-4.04 (m, 1H), 3.78 (s, 6H), 3.39 (app dd, 1H, J=10, 4.5 Hz), 3.33 (app dd, 1H, J=10, 5.0 Hz), 2.50 (ddd, 1H, J=13.5, 6.0, 2.5 Hz), 2.34 (s, 3H), 1.87-1.82 (m, 1H); $^{13}$C NMR (CDCl$_3$, ppm) 158.7, 145.0, 141.0, 138.7, 136.1, 134.3, 130.7, 130.3, 128.3, 128.1, 127.0, 124.5, 119.9, 113.4, 86.2, 78.6, 74.6, 64.4, 55.5, 42.7, 22.6; HRMS (FAB+, NBA matrix) calcd mass 689.0514 for [C$_{33}$H$_{32}$Br$_2$O$_5$]. Found 689.0534.

1',2'-Dideoxy-β-1'-(2,4-dibromo-5-methylphenyl)-5'-O-(4,4'-dimethoxytrityl)-D-ribofuranose cyanoethyl N,N-diisopropylphosphoramidite (3b). $^1$H NMR (CDCl$_3$, ppm) 7.87 (app d, 1H, J=5.0 Hz), 7.50-7.47 (m, 2H), 7.40-7.36 (m, 4H), 7.32-7.25 (m, 2H), 7.23-7.19 (m, 2H), 6.87-6.82 (m, 4H), 5.32 (app quintet, 1H, J=5 Hz, H1'), 4.47-4.40 (m, 1H, H3'), 4.21 (br, 1H, H4'), 3.87-3.76 (m, 1H), 3.79 (app d, 6H, J=3.5 Hz, OCH$_3$), 3.68-3.52 (m, 3H), 3.39-3.26 (m, 2H), 2.69-2.55 (m, 1H, H2'), 2.61 (app t+d, 1H, J=6.5 (for triplet), 1.5 (for doublet) Hz), 2.43 (app t+d, 1H, J=6.5 (for triplet), 1.0 (for doublet) Hz), 2.35 (s, 3H, ArCH$_3$), 1.84-1.78 (m, 1H, H2'), 1.18-1.15 (m, 8H), 1.05 (app d, 4H, J=6.5 Hz); $^{13}$C NMR (CDCl$_3$, ppm) 158.7 (t), 145.1 (d), 140.9 (d), 138.8 (d), 136.2 (t), 134.4 (d), 130.8 (d), 130.4 (q), 128.5 (d), 128.1 (d), 127.0 (d), 124.6 (d), 120.0, 117.8 (d), 113.4, 86.5, 86.0, 85.7 (d), 79.0 (d), 75.8 (d), 64.2 (d), 58.6 (m), 55.5 (d), 43.5 (m), 42.1, 34.9, 31.9, 25.5, 24.8 (m), 22.8 (d), 20.6 (d), 20.4 (d), 14.4; HRMS (FAB+, NBA matrix) calcd mass 889.1592 for [C$_{42}$H$_{49}$Br$_2$N$_2$O$_6$P]. Found 889.1597.

1',2'-Dideoxy-β-1'-(2,4-diiodo-5-methylphenyl)-5'-O-(4,4'-dimethoxytrityl)-D-ribofuranose (4a). $^1$H NMR (CDCl$_3$, ppm) 8.00 (s, 1H), 7.64 (s, 1H), 7.48 (d, 2H, J=7.2 Hz), 7.39-7.36 (m, 4H), 7.30 (app t, 2H, J=7.6 Hz), 7.23-7.19 (m, 1H), 6.85 (dd, 4H, J=7.2, 2.4 Hz), 5.18 (dd, 1H, J=9.6, 6.0 Hz), 4.37-4.34 (m, 1H), 4.06-4.03 (m, 1H), 3.79 (s, 6H), 3.37 (app d, 2H, J=4.4 Hz), 2.51 (ddd, 1H, J=13.2, 6.0, 2.4 Hz), 2.35 (s, 3H), 1.85-1.78 (m, 1H); $^{13}$C NMR (CDCl$_3$, ppm) 158.7, 145.0, 143.9, 142.6, 139.6, 136.9, 136.1, 130.3, 128.3, 128.1, 127.0, 113.4, 101.6, 96.1, 86.6, 86.4, 74.4, 64.3, 55.4, 42.9, 27.4; HRMS (MALDI+, CHCA) calcd mass 785.0229 for [C$_{33}$H$_{32}$I$_2$O$_5$+Na]. Found 785.0260.

1',2'-Dideoxy-β-1'-(2,4-diiodo-5-methylphenyl)-5'-O-(4,4'-dimethoxytrityl)-D-ribofuranose cyanoethyl N,N-diisopropylphosphoramidite (4b). $^1$H NMR (CDCl$_3$, ppm) 8.08 (app d, 1H, J=2.4 Hz), 7.65 (s, 1H), 7.49 (app t, 2H, J=6.0 Hz), 7.41-7.37 (m, 4H), 7.33-7.28 (m, 2H), 7.23-7.19 (m, 1H), 6.86 (dd, 4H, J=8.8, 6.4 Hz), 5.17 (app quintet, 1H, J=4.4 Hz, H1'), 4.48-4.39 (m, 1H), 4.20 (br, 1H), 3.88-3.80 (m, 1H), 3.79 (app d, 6H, J=2.8 Hz, OCH$_3$), 3.76-3.56 (m, 3H), 3.43-3.35 (m, 1H), 3.29-3.24 (m, 1H), 2.71-2.55 (m, 1H, H2'), 2.62 (app t, 1H, J=6.8 Hz), 2.43 (app t, 1H, J=6.4 Hz), 2.36 (s, 3H, ArCH$_3$), 1.18-1.16 (m, 8H), 1.83-1.73 (m, 1H, H2'), 1.05 (app d, 4H, J=7.2 Hz); $^{13}$C NMR (CDCl$_3$, ppm) 158.7, 145.1 (d), 143.6 (d), 142.7, 139.7, 137.0 (d), 136.2 (q), 130.4 (q), 127.0 (d), 117.7 (d), 113.4, 101.7 (d), 96.2, 86.3 (m), 83.0 (d), 75.8 (d), 64.1 (d), 58.6 (q), 55.5, 43.5 (q), 42.3, 31.8, 27.5, 24.8 (t), 22.9, 20.5 (q); HRMS (FAB+, NBA matrix) calcd mass 962.1405 for [C$_{42}$H$_{49}$I$_2$N$_2$O$_6$P]. Found 962.1445.

EXAMPLE 3

Probing the Active Site Tightness of DNA Polymerase in Sub-angstrom Increments

Materials and Methods

Nucleotide analogs. Modified nucleoside analogs were prepared as described above, and the 5'-triphosphate derivatives were prepared and characterized by standard procedures.

Modified oligonucleotides. Phosphoramidite derivatives of the modified nucleosides were prepared as described above. DNA sequences containing modified bases were prepared following the literature procedure.

In vitro steady-state kinetics. As polymerase substrates we used 28 mer/23 mer template-primer duplexes having the sequence (5'-ACT GXT CTC CCT ATA GTG AGT CGT ATT A [SEQ ID NO:1])·(5'-TAA TAC GAC TCA CTA TAG GGA GA [SEQ ID NO:2]). Kinetics were measured at 37° C. in a buffer containing 10 mM Mg$^{2+}$. Buffer details are given in the Table legend. The primer was 5' end-labeled and was extended by the polymerase in the presence of a single dNTP species over varied concentration and time. Products of single nucleotide insertions were resolved from unreacted primer by 20% denaturing gel electrophoresis, and were quantitated by autoradiography. Details of the kinetics experiments are given in the Supporting Data.

Bacterial replication assay. The assay for bypass efficiency fidelity is briefly described in the text.

Results and Discussion

We sought to test the active site tightness hypothesis directly and systematically, by preparing a series of nucleobase analogs having gradually increasing size. The nucleosides dH, dF, dL, dB, dI are all shape analogs of thymidine (FIG. 1). Because they have varied substituents at the 2,4 positions (namely, H, F, Cl, Br, I), they vary in size in 0.2-0.4 Angstrom increments, giving a total size difference of 1.0 Å from the smallest to largest. To evaluate the biophysical effects of the steric series in a polymerase active site, we prepared nucleoside triphosphate derivatives of the five compounds, thus allowing them to act as incoming nucleotide analogs of dTTP; conversely, we prepared template DNAs containing the five nucleoside analogs downstream from a primer binding site.

Figure 5:
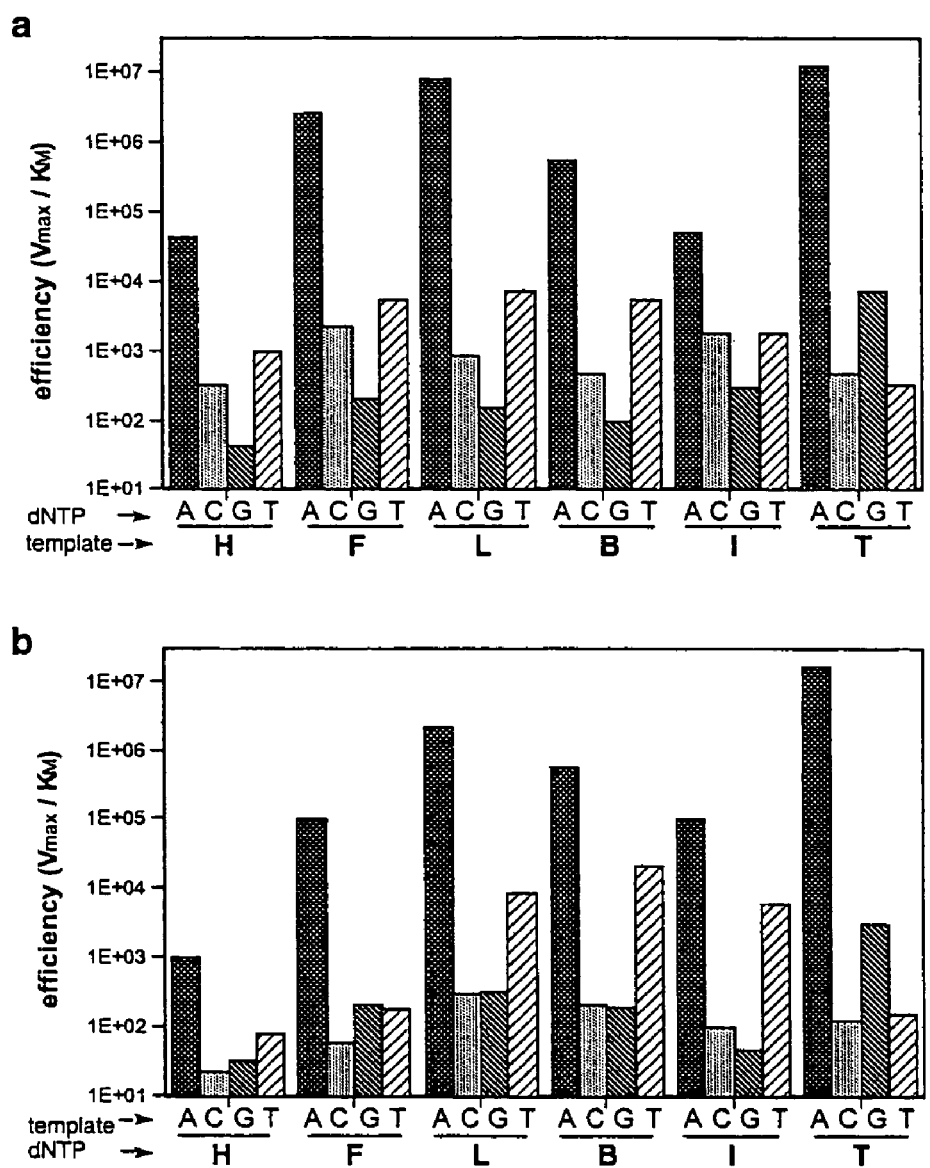
FIG. 5A-5B. Histogram of nucleotide insertion efficiencies vs. varied base pair size. Steady-state efficiencies (as $V_{max}/K_M$) using DNA Pol I (exo-) are shown on a log scale. (a) Insertion of natural nucleotides opposite template base analogs of increasing size (with a template T for comparison). (b) Insertion of nucleoside triphosphate analogs of increasing size, with data for the natural dTTP shown for comparison. Template-primer duplexes had the sequence (5'-ACT GXT CTC CCT ATA GTG AGT CGT ATT A [SEQ ID NO:1])·(5'-TAA TAC GAC TCA CTA TAG GGA GA [SEQ ID NO:2]). Kinetics were measured at 37° C. in a buffer containing 10 mM $Mg^{2+}$. Buffer details are given in the Table legend. The primer was 5' end-labeled and was extended by the polymerase in the presence of a single dNTP species over varied concentration and time. Products of single nucleotide insertions were resolved from unreacted primer by 20% denaturing gel electrophoresis, and were quantitated by autoradiography.

We chose DNA polymerase I (Klenow fragment, exonuclease-deficient) as an ideal candidate for initial study, as it is enzymatically well-characterized among replicative enzymes, and yet is relatively small and acts as a single subunit. We carried out kinetics studies of single nucleotide insertions in the steady state, using a gel electrophoresis-based assay. Kinetic data are given in Tables 4 and 5; the first shows results for insertion of natural deoxynucleoside triphosphates (dNTPs) in separate experiments opposite each of the five analogs in a template strand. Table 5 shows the opposite case: insertion of compounds dH, dF, dL, dB, dI as dNTP analogues opposite the natural template bases A, C, T, or G. As a reference, we compared the results with parallel data for natural thymidine as dTTP (the incoming nucleotide) and dT, the natural nucleoside template (FIG. 1). FIG. 5 shows all the efficiency data in a histogram comparison.

TABLE 4

Steady-state kinetic efficiencies for single nucleotide insertions by DNA Poll (Klenow fragment, exo-). The template contained variable-size thymidine analogues.[a]

| dNTP | template base | $V_{max}^{b}$ (% · m in$^{-1}$) | $K_M$ (µM) | efficiency, $V_{max}/K_M$ | rel. efficiency[c] |
|---|---|---|---|---|---|
| dATP | H | 0.90 ± 0.18 | 20 ± 2 | 4.5 × 10$^4$ | 3.5 × 10$^{-3}$ |
| | F | 24 ± 3 | 9.4 ± 2.9 | 2.6 × 10$^6$ | 2.0 × 10$^{-1}$ |
| | L | 27 ± 5 | 3.3 ± 2.8 | 8.2 × 10$^6$ | 6.3 × 10$^{-1}$ |
| | B | 12 ± 1 | 21 ± 5 | 5.7 × 10$^5$ | 4.4 × 10$^{-2}$ |
| | I | 1.3 ± 0.2 | 26 ± 11 | 5.0 × 10$^4$ | 3.8 × 10$^{-3}$ |
| | T | 24 ± 1 | 1.9 ± 0.5 | 1.3 × 10$^7$ | 1 |
| dGTP | H | 0.025 ± 0.007 | 600 ± 210 | 4.2 × 10$^1$ | 3.2 × 10$^{-6}$ |
| | F | 0.0071 ± 0.0008 | 36 ± 12 | 2.0 × 10$^2$ | 1.5 × 10$^{-5}$ |
| | L | 0.029 ± 0.007 | 190 ± 90 | 1.5 × 10$^2$ | 1.2 × 10$^{-5}$ |
| | B | 0.023 ± 0.005 | 220 ± 100 | 1.0 × 10$^2$ | 7.7 × 10$^{-6}$ |
| | I | 0.017 ± 0.001 | 58 ± 18 | 2.9 × 10$^2$ | 2.2 × 10$^{-5}$ |
| | T | 0.41 ± 0.15 | | 7.3 × 10$^3$ | 5.6 × 10$^{-4}$ |
| dCTP | H | 0.031 ± 0.006 | 100 ± 60 | 3.1 × 10$^2$ | 2.4 × 10$^{-5}$ |
| | F | 0.071 ± 0.011 | 33 ± 11 | 2.2 × 10$^3$ | 1.7 × 10$^{-4}$ |
| | L | 0.021 ± 0.003 | 25 ± 13 | 8.4 × 10$^2$ | 6.5 × 10$^{-5}$ |
| | B | 0.038 ± 0.005 | 79 ± 33 | 4.8 × 10$^2$ | 3.7 × 10$^{-5}$ |
| | I | 0.036 ± 0.001 | 20 ± 8 | 1.8 × 10$^3$ | 1.4 × 10$^{-4}$ |
| | T | 0.022 ± 0.006 | 46 ± 28 | 4.8 × 10$^2$ | 3.7 × 10$^{-5}$ |
| dTTP | H | 0.062 ± 0.022 | 61 ± 37 | 10 × 10$^3$ | 7.7 × 10$^{-5}$ |
| | F | 0.12 ± 0.03 | 22 ± 13 | 5.5 × 10$^3$ | 4.2 × 10$^{-4}$ |
| | L | 0.13 ± 0.04 | 18 ± 18 | 7.2 × 10$^3$ | 5.5 × 10$^{-4}$ |
| | B | 0.20 ± 0.03 | 37 ± 12 | 5.4 × 10$^3$ | 4.2 × 10$^{-4}$ |
| | I | 0.085 ± 0.037 | 48 ± 39 | 1.8 × 10$^3$ | 1.4 × 10$^{-4}$ |
| | T | 0.012 ± 0.004 | 38 ± 38 | 3.2 × 10$^2$ | 2.5 × 10$^{-5}$ |

[a]Conditions: 5 µM template-primer DNA, 0.005 or 0.1 units/µL enzyme, 50 mM Tris.HClbuffer (pH 7.5), 10 mM MgCl$_2$, 1 mM dithiothreito 1, 50 µg/mL bovineserum albumin, 37° C.
[b]Normalized to the lowest enzyme concentration used.
[c]Relative to insertion of dATP opposite T.

TABLE 5

Steady-state kinetic efficiencies for single nucleotide insertions by DNA Poll (Klenow fragment, exo-). Incoming nucleotide analogues of variable size were used.[a]

| dNTP | template base | $V_{max}^{b}$ (% · min$^{-1}$) | $K_M$ (µM) | efficiency, $V_{max}/K_M$ | rel. efficiency[c] |
|---|---|---|---|---|---|
| dHTP | A | 0.11 ± 0.20 | 110 ± 20 | 1.0 × 10$^3$ | 6.3 × 10$^{-5}$ |
| dFTP | | 2.9 ± 0.1 | 29 ± 10 | 1.0 × 10$^5$ | 6.3 × 10$^{-3}$ |
| dLTP | | 39 ± 4 | 18 ± 5 | 2.2 × 10$^6$ | 1.4 × 10$^{-1}$ |
| dBTP | | 13 ± 2 | 23 ± 6 | 5.7 × 10$^5$ | 3.6 × 10$^{-2}$ |
| dITP | | 1.8 ± 0.1 | 18 ± 2 | 1.0 × 10$^5$ | 6.3 × 10$^{-3}$ |
| dTTP | | 30 ± 3 | 1.9 ± 0.4 | 1.6 × 10$^7$ | 1 |
| dHTP | G | 0.0065 ± 0.0016 | 200 ± 90 | 3.3 × 10$^1$ | 2.0 × 10$^{-6}$ |
| dFTP | | 0.0067 ± 0.0017 | 300 ± 120 | 2.2 × 10$^1$ | 1.4 × 10$^{-6}$ |
| dLTP | | 0.035 ± 0.004 | 110 ± 30 | 3.2 × 10$^2$ | 2.0 × 10$^{-5}$ |
| dBTP | | 0.0094 ± 0.0004 | 50 ± 10 | 1.9 × 10$^2$ | 1.2 × 10$^{-5}$ |
| dITP | | 0.0020 ± 0.0001 | 43 ± 7 | 4.7 × 10$^1$ | 2.9 × 10$^{-6}$ |
| dTTP | | 0.42 ± 0.18 | 140 ± 86 | 3.0 × 10$^3$ | 2.5 × 10$^{-4}$ |
| dHTP | C | 0.0067 ± 0.0023 | 310 ± 170 | 2.2 × 10$^1$ | 1.4 × 10$^{-6}$ |
| dFTP | | 0.012 ± 0.004 | 200 ± 110 | 6.0 × 10$^1$ | 3.8 × 10$^{-6}$ |
| dLTP | | 0.050 ± 0.010 | 160 ± 66 | 3.1 × 10$^2$ | 1.9 × 10$^{-5}$ |
| dBTP | | 0.016 ± 0.001 | 74 ± 22 | 2.2 × 10$^2$ | 1.4 × 10$^{-5}$ |
| dITP | | 0.0023 ± 0.0004 | 23 ± 1 | 1.0 × 10$^2$ | 6.3 × 10$^{-6}$ |
| dTTP | | 0.067 ± 0.040 | 510 ± 400 | 1.3 × 10$^2$ | 6.3 × 10$^{-6}$ |
| dHTP | T | 0.0046 ± 0.0011 | 59 ± 27 | 7.8 × 10$^1$ | 4.9 × 10$^{-6}$ |
| dFTP | | 0.0066 ± 0.0010 | 37 ± 15 | 1.8 × 10$^2$ | 1.1 × 10$^{-5}$ |
| dLTP | | 0.54 ± 0.10 | 62 ± 21 | 8.7 × 10$^3$ | 5.4 × 10$^{-4}$ |
| dBTP | | 0.8 ± 0.16 | 38 ± 21 | 2.1 × 10$^4$ | 1.3 × 10$^{-3}$ |
| dITP | | 0.23 ± 0.02 | 37 ± 7 | 6.2 × 10$^3$ | 3.9 × 10$^{-4}$ |
| dTTP | | 0.010 ± 0.002 | 63 ± 18 | 1.6 × 10$^2$ | 1.0 × 10$^{-5}$ |

[a]Conditions: 5 µM template-primer DNA, 0.005 or 0.1 units/µL enzyme, 50 mM Tris•HCl buffer (pH 7.5), 10 mM MgCl$_2$, 1 mM dithiothreitol, 50 µg/mL bovine serum albumin, 37° C.
[b]Normalized to the lowest enzyme concentration used.
[c]Relative to insertion of dTTP opposite A.

Kinetic efficiency was measured as $V_{max}/K_M$ for nucleotide insertions at 37° C. A comparison of efficiencies for the steric series in the template with insertion of natural dATP (the presumably preferred partner) showed that as size increased from the hydrogen to fluorine to chlorine analogues, a total increase of 0.66 Å, efficiency increased markedly, by a factor of 180. The data are compared graphically with respect to relative size in FIG. 6a. Surprisingly, the Cl-substituted analog, whose "base" is larger than thymine by 0.5 Å, is the most efficient of the entire series. The efficiency with this chlorinated thymidine analog is the same within experimental error as that with the natural template, dT, despite the nonpolar nature of dL. With increasing size beyond the dichloro-substituted compound (dB and dI respectively), the efficiency dropped markedly, by a factor of 164-fold for the largest, in response to a subtle size increase of only 0.35 Å over the optimum.

The converse experiments, measuring efficiency for dNTP analog insertion opposite natural adenine in the template, showed very similar results (Table 4 and FIG. 5b). Once again, efficiency increased with size until a maximum was reached, and then it dropped with further size increases, showing a large range of 2200-fold in activity (see plot in FIG. 6b). The chlorinated dNTP was inserted opposite adenine with greatest efficiency, and the efficiency was only 7-fold lower than for insertion of natural dTTP, again despite the fact that the chlorinated compound is larger than dTTP by 0.5 Å. The change from chlorine to bromine to iodine in the template base (a size difference of 0.35 Å) caused a 22-fold drop in efficiency, apparently reflecting the steep potential energy function of a steric effect in the active site.

Figure 7:
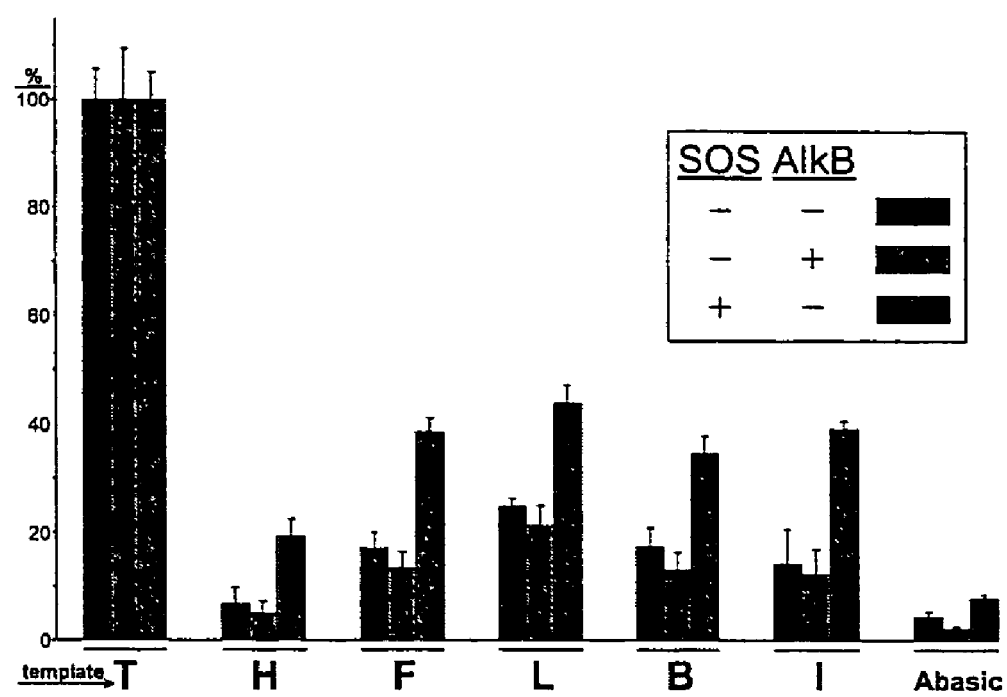
FIG. 7. Replication bypass efficiency of varied-size thymidine analogs by normal and bypass (SOS-induced) polymerases in *E. coli*. The trans-analog DNA synthesis experiment was performed in triplicate, with one standard deviation shown.

We also evaluated fidelity systematically by comparing correctly matched and mismatched pairs across this series. The efficiency of each correctly matched A-T analog pair was divided by the efficiency for enzymatic synthesis of the corresponding mismatched T-T analog pair, which is the most efficient mismatch, thus defining fidelity. The most efficient mismatches with the nonpolar thymine mimics were those opposite T, consistent with previous studies, while natural thymidine is most frequently mispaired with guanine. The fidelity data are plotted graphically with respect to size in FIGS. 7c and 7d.

The results for varied-size template nucleoside mimics showed that fidelity increased with increasing size from the smallest compound, and reached a maximum at the dichloro compound. The magnitude of increase in fidelity was large: the fidelity with the smallest (dH) compound was only 45, while with dL it was 1100. This apparently optimally-sized compound displayed fidelity that was within experimental error of that for natural thymidine. As size increased further, the fidelity then dropped markedly (by a factor of 40 for a size increase of 0.35 Å from dL to dI). Thus the size effects on fidelity closely mirrored those seen for efficiency, suggesting a direct relationship between the physical origins of both effects.

Figure 6:
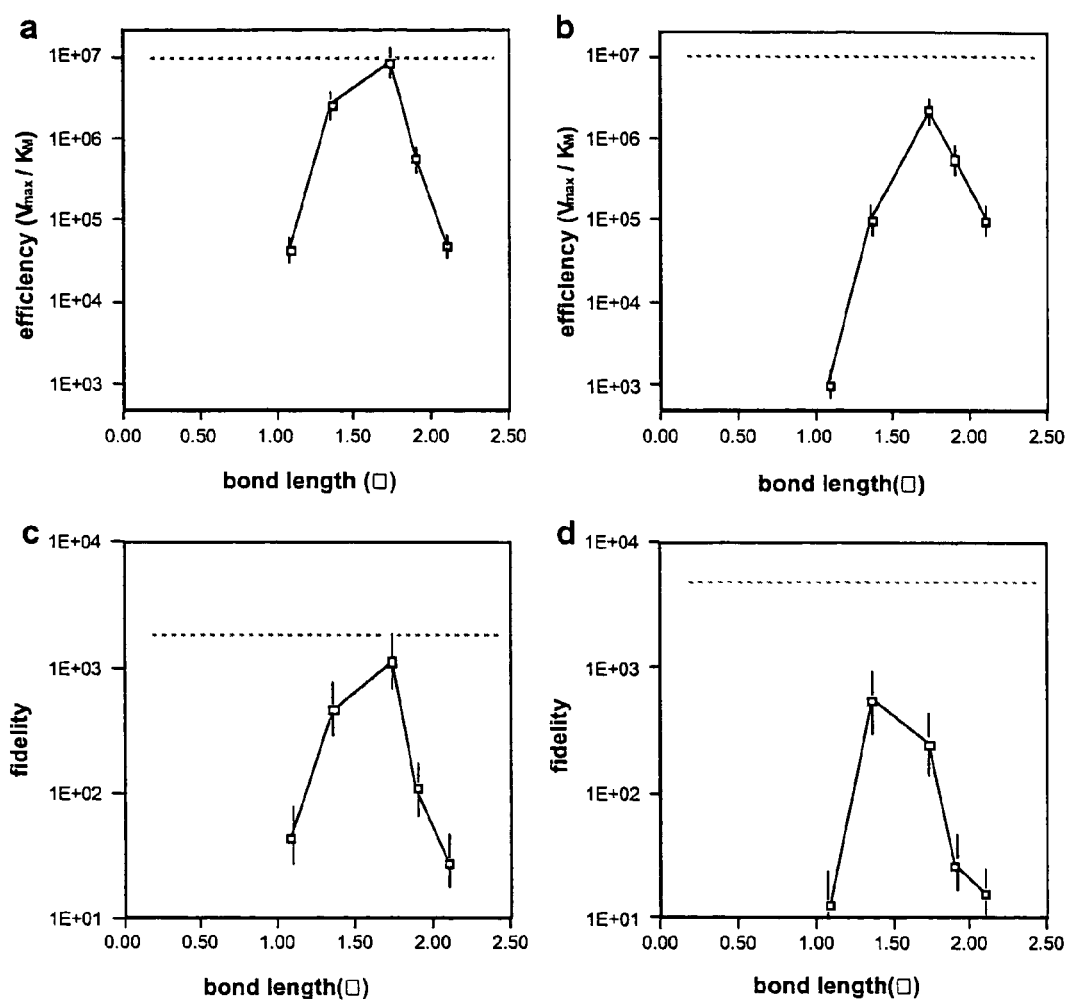
FIG. 6A-6D. The effects of expanding base pair size in a polymerase active site, shown by plotting thymidine analog bond lengths (the variable bond) versus efficiency and fidelity. (a) Efficiency for insertion of natural dATP as a function of template bond lengths; varied thymidine mimics (H,F,L,B,I) are in the template. (b) Efficiency for insertion of varied-size dNTPs (as a function of bond lengths) against adenine in the template. (c) Fidelity for insertion of natural dATP (rather than dCTP, dGTP, or dTTP) opposite template thymine analogs of increasing size. Fidelity was defined as efficiency for the correct T analog: A pair divided by the efficiency of the most efficient mismatch. (d) Selectivity for insertion of thymidine nucleotide analogs opposite a template A (rather than C, G, or T) as a function of incoming nucleotide size. Dashed line in each plot shows the value for the corresponding natural T-A/A-T base pair.

The converse experiments, evaluating fidelity effects with increasing dNTP size, were similar, although not identical (see Table 5 and FIG. 6d). In this case the fidelity maximum was reached at a slightly smaller size, dFTP, instead of dLTP; these are different by 0.38 Å in bond lengths. Particularly striking in this case was a large increase in fidelity on increasing size from dHTP to dFTP, reflecting a difference of 0.28 Å.

Figure 8:
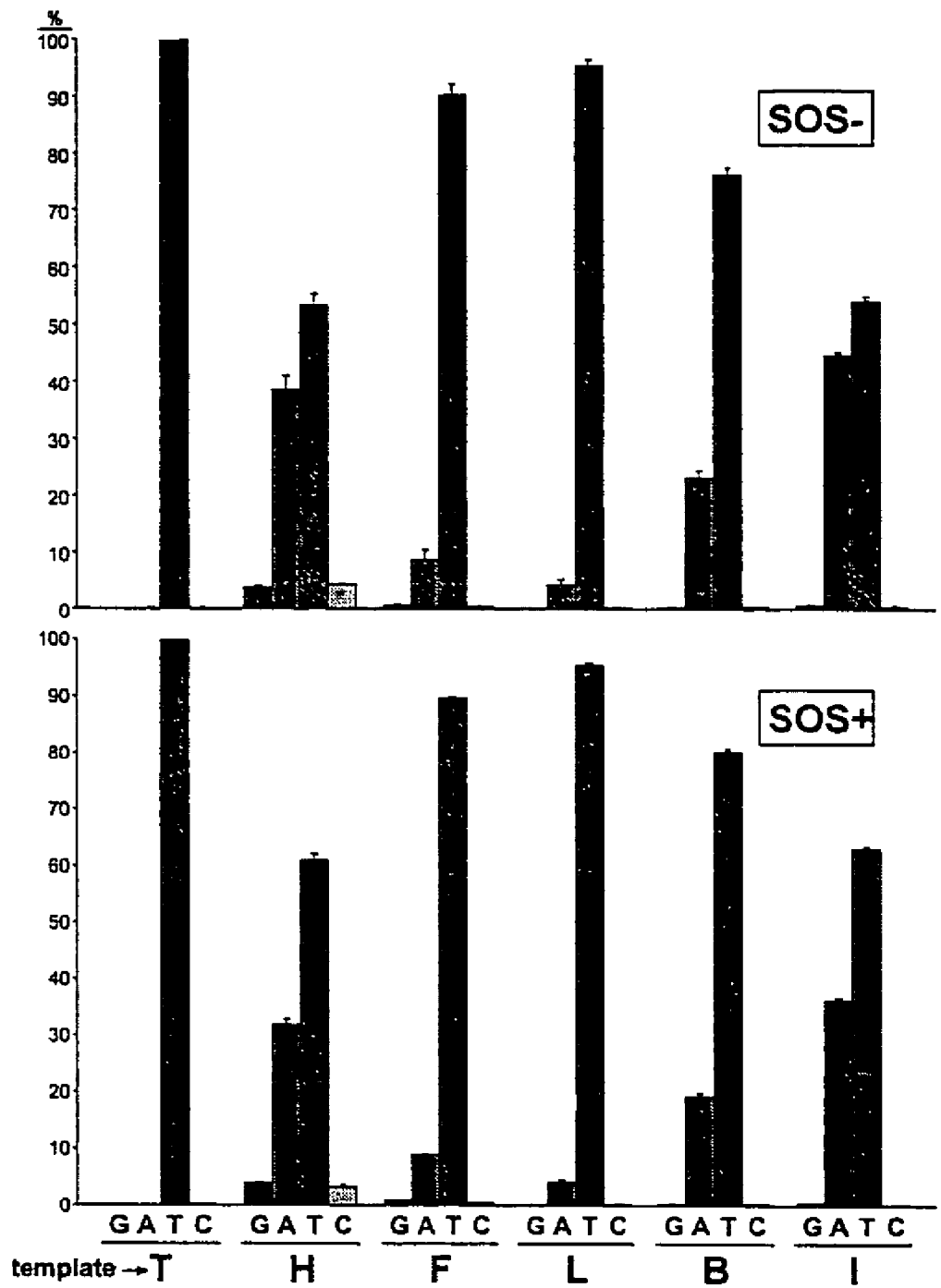
FIG. 8. Fidelity of replication of varied-size thymidine analogs by normal (top) and SOS-induced bypass (bottom) polymerases in *E. coli*. The distribution of G (green), A (red), T (blue) and C (yellow) at the analog site from the phage progeny is shown. Since the analogs function like T in vivo, T replaces them in the progeny. Base compositions were obtained in triplicate as described in the Supporting Material, with one standard deviation shown.

To ascertain the influence of sub-Angstrom size increases on the template coding properties of the T analogs in vivo, we ligated oligonucleotides containing each analog into a single-stranded M13 vector, which were then passaged through *E. coli* and scored for bypass efficiency and mutagenesis (fidelity) as described. We chose *E. coli* deficient in AlkB to eliminate the possibility of metabolization of the H analog, which was subsequently found to have no influence on the results when compared with AlkB-proficient cells. Bypass experiments shown in FIG. 7 were performed in a competitive manner, and efficiencies were evaluated by PCR-based quantitation of successfully replicated progeny DNA. SOS-induction of bypass polymerases by prior irradiation of *E. coli* with ultraviolet light increased trans-analog synthesis approximately 2-fold for all thymine analogs. While all five analogs hindered the progression of both the normal and bypass polymerases, the bell-shaped histograms for the different cell types were similar to the above in vitro Pol I (Klenow fragment) studies, with maximum bypass for the L (dichloro) analog. Likewise, the replication fidelity experiments in *E. coli* shown in FIG. 8 depict bell-curves for the normal and bypass polymerases with maximal in vivo fidelity for the analog L. Single-base deletions were also evident at the size extremes for the analogs H and I, which diminished when bypass polymerases were induced. It is noteworthy that the difference between the match and mismatch efficiency increased in cells expressing induced bypass polymerases: L (0.2), B (8.0), I (17.4), implying higher fidelity for the larger isosteres for bypass polymerases, which may contain larger or looser active sites.

The above experiments give evidence for a number of significant mechanistic aspects of DNA replication. First, as they increase in bulk, base pairs can clearly reach a size where they are rejected as efficient substrates. This confirms the importance of steric rejection of many DNA lesions that increase nucleobase size, such as methylated bases and exocyclic adducts. Our data show that this rejection begins to be seen at size increases that are smaller than known DNA lesions. For example, with a small ~0.4 Å size increase over the optimum (only about a quarter of a single bond length), we observed a steric rejection amounting to over two orders of magnitude on efficiency, suggesting that DNA base lesions (which are larger) could easily achieve biologically relevant rejection levels with steric effects alone. The results are also consistent with studies involving deoxyribose variants with substituents added at the 4' position, where too-large substitutions showed lowered polymerase activity.

Second, our observation that efficiency increases markedly with pair size up to the maximum suggests that there is a positive energetic influence of size (and/or a negative influence of insufficient size) at the transition state for phosphodiester bond formation. This may be due to two factors: first, unfilled voids are energetically unfavorable in aqueous solution; and second, a too-small size may lead to an incorrect positioning of the triphosphate moiety for phosphodiester bond formation. Natural base pairings that are smaller than the canonical Watson-Crick size, such as pyrimidine-pyrimidine mispairs, might easily be rejected by such mechanisms. Importantly, we observe that the natural base pair size is less than optimum in efficiency for Pol I (and indeed, for the replication machinery in intact *E. coli*), which demonstrated an efficiency maximum at a size almost one Angstrom larger than a Watson-Crick pair taking into account hydrogen bonding contraction (see below). This is consistent with recent observations that low fidelity and low efficiency tend to correlate in the known DNA polymerases. If low fidelity is caused by a large active site, then the unfilled volume associated with this should lower efficiency, as observed here with the smallest substrate sizes. Note that the current experiments would not distinguish between the physical resting space in the polymerase active site, and induced space, whereby larger substrates might be accommodated by low-thermodynamic-cost movements of sidechains or helices in the enzyme. Thus we define the current steric space as the "functional space" rather than necessarily as a defined, static void; future structural studies of polymerases at high resolution may help in making this distinction.

It is worthwhile to consider whether other chemical and physical factors in this nucleotide series might explain these results. For example, hydrophobicity and stacking propensity also change with increasing size. However, the changes in these two properties are relatively small across the series, and increase from smallest to largest, a trend that clearly does not correlate with the observed effects. One may also consider possible electrostatic effects, since the electronegativity of the substituents also varies. The results show a relatively poor correlation; for example, hydrogen is electropositive relative to carbon while iodine is neutral, yet the analogs containing them have similar activities. In addition, the difluoro analog has a considerably higher net dipole than the dichloro case; but the dichlorinated species is considerably more active. Previous studies with compounds having stronger net dipoles have also failed to note an effect with Pol I. Thus the data not well explained by these effects, and are most consistent with the sized-based hypothesis.

The results have important implications in the mechanisms of fidelity in replicative DNA polymerases. Our observations of increasing fidelity with increasing size suggest that active site steric tightness is an important factor contributing to this selectivity. Increases in size from the smallest substrates to the optimum yielded substantial increases in fidelity, underscoring the need to fill the available active site space before steric differences between matched and mismatched partners can be discriminated. Second, the observation that fidelity is lost when pairs are too large, even by a small amount, is also consistent with a "tight active site" model; if the pair cannot be accommodated in appropriate side-by-side fashion in the active site, then the enzyme cannot exert the influence of a steric wall to constrain the pair's structure. Thus, both correct pairs (involving too-large thymidine analogs) and mispairs are similarly rejected. We observed that size increases much smaller than would be the case for most lesions or mispairs led to substantial losses in fidelity, which suggests that steric effects may be sufficient to explain most or all of this replicative enzyme's observed fidelity with natural base pairs.

A final, and initially somewhat surprising, conclusion from these experiments is that natural Watson-Crick pairs appear to be smaller than optimum for this enzyme, both in terms of efficiency and fidelity. Taking into account the hydrogen bonding contraction, models suggest that a T-A pair is 0.5-0.7 Å smaller than the optimum measured here (the L-A pair without contraction). This suggests that Pol I has an active site that is 0.5-0.7 Å larger than is ideal, and that such a replicative polymerase might be rendered more efficient and yield higher fidelity than it does, if it could evolve an active site that were sterically more constricted by this amount. We presume that such a structure is possible in a folded protein, and we therefore suggest that the lack of optimum tightness likely arises for evolutionary reasons. We hypothesize that selection pressures in *E. coli* have yielded a lower fidelity than the maximum in order to confer adaptability that arises from a small but influential mutation rate.

Recent structural studies of low-fidelity DNA polymerases, which function to bypass mispairs or damaged pairs, have suggested greater steric openness at their active sites. Low-fidelity polymerases are known to have low efficiency as well, consistent with the current observations in the Pol I active site. The current results suggest that a general mechanism for varying fidelity may be simply related to regulation of the sterically allowable sizes of base pairings. This leads to a testable prediction; namely, that the base pair size optimum may be larger or broader than that with a higher fidelity enzyme such as Pol I, and that increasing base pair size in low-fidelity enzymes may increase both their efficiency and fidelity. Studies are underway to test these possibilities. This expanding-size nucleotide series might be generally useful in probing functional steric tightness in a systematic way for enzymes of varying fidelity.

EXAMPLE 4

The Effects of Varied Nucleobase Shape on DNA Replication

Goal: to vary the shape of thymidine analogs in order to evaluate the effect of base shape on a DNA polymerase enzyme.

1 (2C4H)

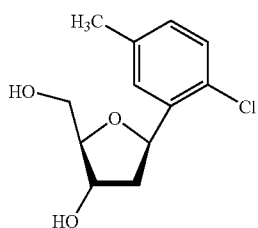

-continued 2 (3C)

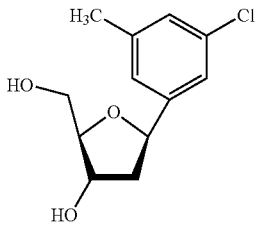

3 (2H4C)

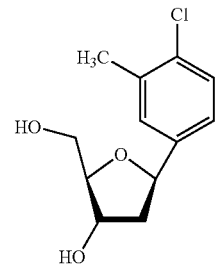

4 (2, 3-di-C)

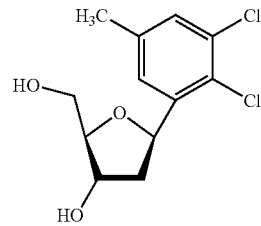

5 (3, 4-di-C)

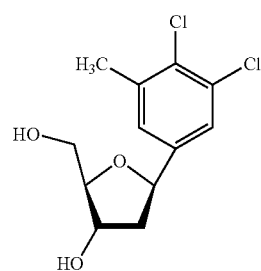

6 (2B4C)

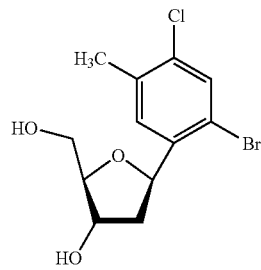

7 (2C4B)

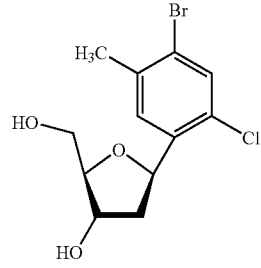

8 (2C4F)

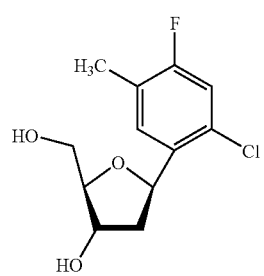

10 (2C4C)

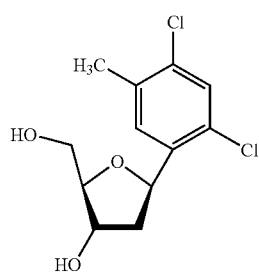

9 (2F4C)

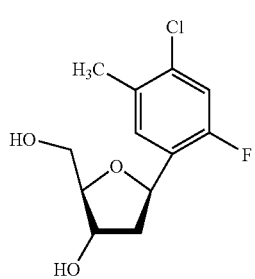

The analogs synthesized and tested in this study. The dXTP variants in part B have a 5' triphosphate group added to these structures.

A. Incorporating dATP Opposite Template Thymidine Analogs

Data for single nucleotide insertion kinetics in the steady-state. The enzyme was the Klenow fragment of DNA pol I from *E. coli* (exonuclease deficient). Methods are as described above.

TABLE 6

Gradually increasing size at position 4

| Template analog | dNTP | $V_{max}$ | $K_m/\mu M$ | efficiency | Rel. efficiency |
|---|---|---|---|---|---|
| T | dATP | 45.7931 ± 1.7743 | 2.60 ± 0.75 | $(1.86 \pm 0.56) \times 10^7$ | 1 |
| 2C4H | dATP | 37.8620 ± 0.9587 | 11.00 ± 0.45 | $(3.43 \pm 0.11) \times 10^6$ | $1.8 \times 10^{-1}$ |
| 2C4F | dATP | 17.7775 ± 0.1689 | 4.01 ± 1.14 | $(4.62 \pm 1.14) \times 10^6$ | $2.5 \times 10^{-1}$ |
| 2C4C | dATP | 64.6879 ± 3.9292 | 8.29 ± 2.33 | $(8.14 \pm 1.81) \times 10^6$ | $4.4 \times 10^{-1}$ |
| 2C4B | dATP | 30.4709 ± 0.8544 | 4.18 ± 0.47 | $(7.38 \pm 1.07) \times 10^6$ | $4.0 \times 10^{-1}$ |

TABLE 7

Gradually increasing size at 2-position

| Template base | dNTP | $V_{max}$ | $K_m/\mu M$ | efficiency | Rel. efficiency |
|---|---|---|---|---|---|
| T | dATP | 45.7931 ± 1.7743 | 2.60 ± 0.75 | $(1.86 \pm 0.56) \times 10^7$ | 1 |
| 2H4C | dATP | 2.8214 ± 0.5396 | 31.50 ± 8.91 | $(9.81 \pm 1.58) \times 10^4$ | $5.3 \times 10^{-3}$ |
| 2F4C | dATP | 49.7002 ± 1.5432 | 7.51 ± 2.79 | $(7.13 \pm 2.13) \times 10^6$ | $3.8 \times 10^{-1}$ |
| 2C4C | dATP | 64.6879 ± 3.9292 | 8.29 ± 2.33 | $(8.14 \pm 1.81) \times 10^6$ | $4.4 \times 10^{-1}$ |
| 2B4C | dATP | 1.6202 ± 0.0624 | 3.81 ± 0.01 | $(4.26 \pm 0.16) \times 10^5$ | $2.3 \times 10^{-2}$ |

TABLE 8

Substituting position-3

| Template | dNTP | $V_{max}$ | $K_m/\mu M$ | efficiency | Rel. efficiency |
|---|---|---|---|---|---|
| T | dATP | 45.7931 ± 1.7743 | 2.6 ± 0.7 | $(1.86 ± 0.56) \times 10^7$ | 1 |
| 2C4C | dATP | 64.6879 ± 3.9292 | 8.29 ± 2.33 | $(8.14 ± 1.81) \times 10^6$ | $4.4 \times 10^{-1}$ |
| 3,4-di-C | dATP | 0.4291 ± 0.1095 | 55.0 ± 24.0 | $(8.30 ± 1.55) \times 10^3$ | $4.5 \times 10^{-4}$ |
| 2,3-di-C | dATP | 0.5635 ± 0.2999 | 27.2 ± 14.9 | $(2.14 ± 0.33) \times 10^4$ | $1.2 \times 10^{-3}$ |
| 3C | dATP | 0.4378 ± 0.1116 | 51.9 ± 1.9 | $(8.62 ± 0.85) \times 10^3$ | $4.6 \times 10^{-4}$ |

Summary: For acting as an efficient analog of thymidine in a template strand for replication and amplification, the optimum size for the 4-position group is chlorine or bromine. At the 2-position, the optimum size is chlorine or fluorine. The most efficient analog overall is the 2-chloro-4-chloro analog (compound 10), although the 2C4B and 2F4C analogs (compounds 9,7 respectively) are probably as good. Substitution of chlorine at the 3-position strongly decreases activity.

B. Incorporating Nonnatural Analogs (dXTP) Opposite Adenine in a DNA Template

TABLE 9

Gradually increasing size at position 4

| Template base | dXTP | $V_{max}$ | $K_m/\mu M$ | efficiency | Rel. efficiency |
|---|---|---|---|---|---|
| A | dTTP | 30.70 ± 12.0 | 1.56 ± 1.0 | $(2.29 ± 0.9) \times 10^7$ | 1 |
| A | 2C4H | 1.86 ± 0.16 | 174 ± 5.9 | $1.07 \times 10^4$ | $4.7 \times 10^{-4}$ |
| A | 2C4F | 14.80 ± 1.8 | 84.4 ± 12.9 | $(1.76 ± 0.06) \times 10^5$ | $7.7 \times 10^{-3}$ |
| A | 2C4C | 55.00 ± 0.8 | 33.8 ± 0.6 | $(1.63 ± 0.01) \times 10^6$ | $7.1 \times 10^{-2}$ |
| A | 2C4B | 65.80 ± 4.3 | 29.2 ± 1.5 | $(2.25 ± 0.09) \times 10^6$ | $9.8 \times 10^{-2}$ |

TABLE 10

Gradually increasing 2-position size

| Template base | dNTP | $V_{max}$ | $K_m/\mu M$ | efficiency | Rel. efficiency |
|---|---|---|---|---|---|
| A | dTTP | 30.70 ± 12.0 | 1.56 ± 1.0 | $(2.29 ± 0.9) \times 10^7$ | 1 |
| A | 2H4C | 1.9 ± 0.2 | 176 ± 17 | $(1.08 ± 0.02) \times 10^4$ | $4.7 \times 10^{-4}$ |
| A | 2F4C | 33.9 ± 6.1 | 121 ± 24 | $(2.81 ± 0.06) \times 10^5$ | $1.2 \times 10^{-2}$ |
| A | 2C4C | 55.0 ± 0.8 | 33.8 ± 0.6 | $(1.63 ± 0.01) \times 10^6$ | $7.1 \times 10^{-2}$ |
| A | 2B4C | 17.6 ± 1.6 | 23.8 ± 2.0 | $(7.4 ± 0.4) \times 10^5$ | $3.2 \times 10^{-2}$ |

TABLE 11

Substituting position-3

| Template | dNTP | $V_{max}$ | $K_m/\mu M$ | efficiency | Rel. efficiency |
|---|---|---|---|---|---|
| A | dTTP | 30.70 ± 12.0 | 1.56 ± 1.0 | $(2.29 ± 0.9) \times 10^7$ | 1 |
| A | 2C4C | 55.0 ± 0.8 | 33.8 ± 0.6 | $(1.63 ± 0.01) \times 10^6$ | $7.1 \times 10^{-2}$ |
| A | 3,4-di-C | 1.33 ± 0.05 | 274 ± 9 | $4.90 \times 10^3$ | $2.1 \times 10^{-4}$ |
| A | 2,3-di-C | 0.23 ± 0.01 | 148 ± 10 | $(1.57 ± 0.03) \times 10^3$ | $6.8 \times 10^{-5}$ |
| A | 3C | 0.85 ± 0.08 | 1310 ± 78 | $(6.50 ± 0.20) \times 10^2$ | $2.8 \times 10^{-5}$ |

Summary: For acting as an efficient analog of thymidine triphosphate (as an incoming nucleotide) in replication and amplification, the optimum size for the 4-position group is bromine, with chlorine a close second. At the 4-position, the optimum size is also chlorine, with bromine a close second. The most efficient analog overall is the 2-chloro-4-bromo analog (compound 7 as its 5'-triphosphate derivative), with the 2C4C molecule (cmpd. 10) a close second. Substitution of chlorine at the 3-position strongly decreases activity.

EXAMPLE 5

Synthesis of Radiolabeled Compound

The following synthetic scheme has been used to generate a radiolabeled analog of the dichloro nucleoside. By using different isotopes of iodine, including $^{123}$I, $^{124}$I, $^{125}$I, $^{128}$I and $^{131}$I, the molecule is varied for PET imaging analogs or radiotherapeutic analogs. In an alternative synthesis, an $^{11}$C-labeled methyl group is introduced in the final step of synthesis.

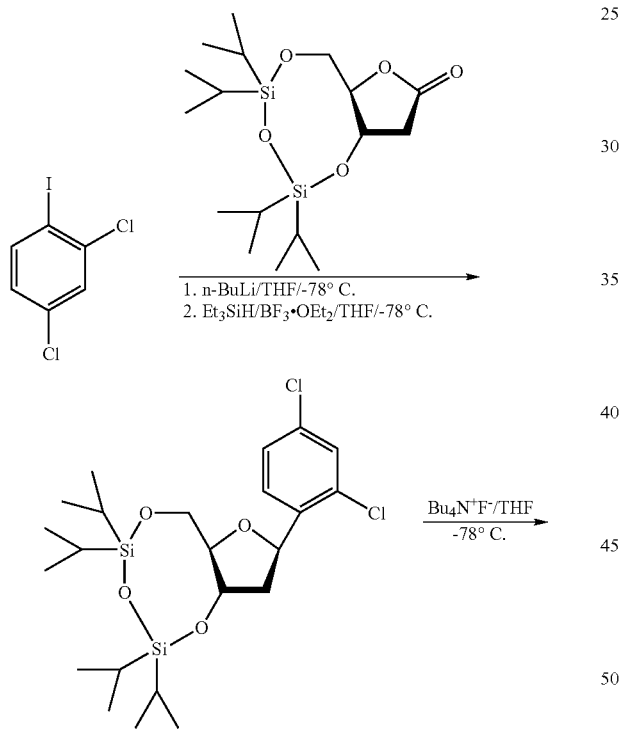

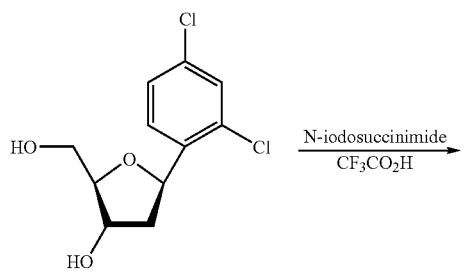

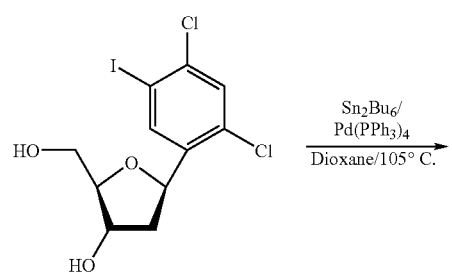

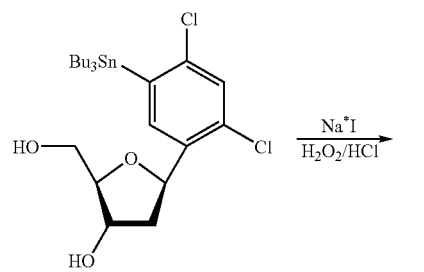

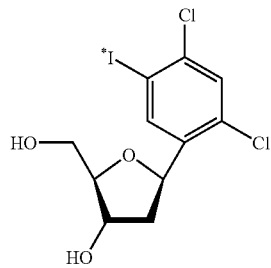

What is claimed is:

1. A nucleoside analog comprising a halogenated base of the structure:

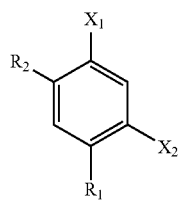

where $R_1$ is a sugar moiety;

$R_2$ is H, $CH_3$, an imaging moiety selected from $^{11}CH_3$, $^{13}N$, $^{15}O$, $^{18}F$, $^{123}I$, $^{124}I$, $^{125}I$, $^{128}I$, $^{111}In$, $^{67}Ga$ and $^{99m}Tc$ or a cytotoxic moiety selected from $^{123}I$, $^{125}I$, $^{131}I$, $^{90}Y$, $^{211}At$, $^{67}Cu$, $^{186}Re$, $^{188}Re$, $^{212}Pb$, and $^{212}Bi$; and $X_1$ and $X_2$ are a combination selected from 2,4-dichloro; 2,4-dibromo; 2-chloro,4-bromo; 2-bromo,4-chloro; 2-bromo,4-fluoro; and 2-fluoro,4-bromo.

2. A nucleotide comprising the nucleoside analog of claim 1.

3. The nucleoside analog of claim 1, wherein the halogenated base is 2-chloro-4-bromo-toluene or 2,4-dichlorotoluene.

4. The nucleoside analog of claim 1, wherein $R_1$ is selected from a ribose, deoxyribose or dideoxyribose sugar modified at one or more of the 2', 3', 4' and 5' positions, which modification terminates polymerization.

5. A polynucleotide comprising at least one nucleoside analog according to claim 1.

6. The polynucleotide according to claim 5, wherein said analog is at one or both terminal positions.

7. The polynucleotide according to claim 5, wherein said analog is at other than a terminal position.

8. A nucleoside analog comprising a halogenated base of the structure:

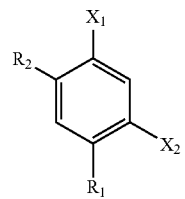

where $R_1$ is a sugar moiety;

$R_2$ is an imaging moiety selected from $^{11}CH_3$, $^{13}N$, $^{15}O$, $^{18}F$, $^{123}I$, $^{124}I$, $^{125}I$, $^{128}I$, $^{111}In$, $^{67}Ga$ and $^{99m}Tc$; and $X_1$ and $X_2$ are independently selected from I, Cl, Br, and F, with the proviso that not more than one F will be present at these positions.

9. The nucleoside analog of claim 8, wherein $R_2$ is selected from $^{11}CH_3$, $^{18}F$, $^{123}I$, $^{124}I$, $^{125}I$ and $^{128}I$.

10. A nucleoside analog comprising a halogenated base of the structure:

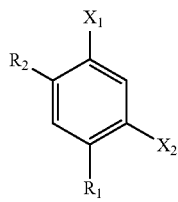

where $R_1$ is a sugar moiety;
$R_2$ is a cytotoxic moiety selected from $^{123}$I, $^{125}$I, $^{131}$I, $^{90}$Y, $^{211}$At, $^{67}$Cu, $^{186}$Re, $^{188}$Re, $^{212}$Pb, and $^{212}$Bi; and
$X_1$ and $X_2$ are independently selected from I, Cl, Br, and F, with the proviso that not more than one F will be present at these positions.

11. A nucleoside analog comprising the structure

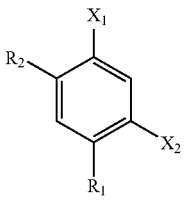

where $R_1$ is a sugar moiety;
$R_2$ is H or $CH_3$; and
$X_1$ and $X_2$ are independently selected from I, Cl, Br, and F, and wherein at least one of $X_1$ and $X_2$ is $^{123}$I, $^{125}$I, $^{131}$I.

12. A pharmaceutical formulation comprising a nucleoside analog according to claim 1 or polynucleotide according to claim 5, and a pharmaceutically acceptable excipient.

13. A method of polynucleotide polymerization, the method comprising:
polymerizing a polynucleotide utilizing as a substrate a nucleotide analog comprising a halogenated base of the structure:

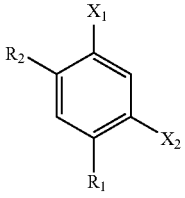

where $R_1$ is a sugar moiety;
$R_2$ is H, $CH_3$, an imaging moiety selected from $^{11}CH_3$, $^{13}$N, $^{15}$O, $^{18}$F, $^{123}$I, $^{124}$I, $^{125}$I, $^{128}$I, $^{111}$In, $^{67}$Ga and $^{99m}$Tc or a cytotoxic moiety selected from $^{123}$I, $^{125}$I, $^{131}$I, $^{90}$Y, $^{211}$At, $^{67}$Cu, $^{186}$Re, $^{188}$Re, $^{212}$Pb, and $^{212}$Bi; and
$X_1$ and $X_2$ are are a combination selected from 2,4-dichloro; 2,4-dibromo; 2-chloro,4-bromo; 2-bromo,4-chloro; 2-bromo,4-fluoro; and 2-fiuoro,4-bromo.

14. The method according to claim 13, the method comprising:
polymerizing a polynucleotide utilizing as a substrate a nucleotide analog comprising a halogenated base selected from 2-chloro-4-bromo-toluene or 2,4-dichlorotoluene.

15. The method according to claim 13, wherein said reaction in performed in vivo.

16. The method according to claim 13, wherein said reaction is performed in vitro.

17. The method according to claim 13, wherein said polymerization reaction is catalyzed by one of DNA dependent DNA polymerase, DNA dependent RNA polymerase, RNA dependent DNA polymerase, and RNA dependent RNA polymerase.

18. The method of claim 13, wherein said reaction is an isothermal amplification reaction.

19. A method of inhibiting polynucleotide polymerization, the method comprising;
polymerizing a polynucleotide utilizing as a substrate a nucleotide analog comprising a halogenated base of the structure:

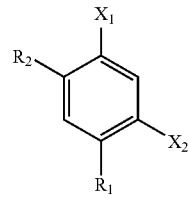

where $R_1$ is a ribose, deoxyribose or dideoxyribose sugar modified at one or more of the 2', 3', 4' and 5' positions with a modification that inhibits polymerization;
$R_2$ is H, $CH_3$, an imaging moiety selected from $^{11}CH_3$, $^{13}$N, $^{15}$O, $^{18}$F, $^{123}$I, $^{124}$I, $^{125}$I, $^{128}$I, $^{111}$In, $^{67}$Ga and $^{99m}$Tc or a cytotoxic moiety selected from $^{123}$I, $^{125}$I, $^{131}$I, $^{90}$Y, $^{211}$At, $^{67}$Cu, $^{186}$Re, $^{188}$Re, $^{212}$Pb, and $^{212}$Bi; and
$X_1$ and $X_2$ are a combination selected from 2,4-dichloro; 2,4-dibromo; 2-chloro,4-bromo; 2-bromo,4-chloro; 2-bromo,4-fluoro; and 2-fiuoro,4-bromo,
wherein polymerization is inhibited by said nucleotide analog.

* * * * *

SEQUENCE LISTING

<160> NUMBER OF SEQ ID NOS: 3

<210> SEQ ID NO 1
<211> LENGTH: 28
<212> TYPE: DNA
<213> ORGANISM: Artificial Sequence
<220> FEATURE:
<223> OTHER INFORMATION: synthetic primer

```
<220> FEATURE:
<221> NAME/KEY: misc_feature
<222> LOCATION: 5
<223> OTHER INFORMATION: n = A,T,C or G

<400> SEQUENCE: 1
actgntctcc ctatagtgag tcgtatta                                                28

<210> SEQ ID NO 2
<211> LENGTH: 23
<212> TYPE: DNA
<213> ORGANISM: Artificial Sequence
<220> FEATURE:
<223> OTHER INFORMATION: synthetic primer

<400> SEQUENCE: 2
taatacgact cactataggg aga                                                     23

<210> SEQ ID NO 3
<211> LENGTH: 12
<212> TYPE: DNA
<213> ORGANISM: Artificial Sequence
<220> FEATURE:
<223> OTHER INFORMATION: synthetic primer that is double stranded DNA
<220> FEATURE:
<221> NAME/KEY: misc_feature
<222> LOCATION: 7
<223> OTHER INFORMATION: n = A,T,C or G

<400> SEQUENCE: 3
cttttcnttc tt                                                                 12
```